US012232902B1

(12) United States Patent
Pollema et al.

(10) Patent No.: US 12,232,902 B1
(45) Date of Patent: Feb. 25, 2025

(54) TARGETING CORONARY REVASCULARIZATION BASED ON MYOCARDIAL VIABILITY

(71) Applicants: The Vektor Group Inc., San Diego, CA (US); The Regents of the University of California, Oakland, CA (US)

(72) Inventors: Travis Pollema, Oakland, CA (US); Gordon Ho, Oakland, CA (US); Robert Joseph Krummen, Bellevue, WA (US); Christopher J. T. Villongco, Oakland, CA (US); Christian David Marton, Jersey City, NJ (US)

(73) Assignees: THE REGENTS OF THE UNIVERSITY OF CALIFORNIA; THE VEKTOR GROUP, INC.

( * ) Notice: Subject to any disclaimer, the term of this patent is extended or adjusted under 35 U.S.C. 154(b) by 0 days.

(21) Appl. No.: 18/739,199

(22) Filed: Jun. 10, 2024

Related U.S. Application Data

(60) Provisional application No. 63/516,862, filed on Aug. 1, 2023.

(51) Int. Cl.
*A61B 6/50* (2024.01)
*A61B 6/00* (2024.01)
(Continued)

(52) U.S. Cl.
CPC ............. *A61B 6/503* (2013.01); *A61B 6/032* (2013.01); *A61B 6/466* (2013.01); *A61B 6/504* (2013.01);
(Continued)

(58) Field of Classification Search
CPC ......... A61B 6/503; A61B 6/032; A61B 6/466; A61B 6/504; A61B 6/507; A61B 6/5217;
(Continued)

(56) References Cited

U.S. PATENT DOCUMENTS

| 5,601,084 A | 2/1997 | Sheehan et al. |
| 10,734,096 B1 | 8/2020 | Neumann |

(Continued)

FOREIGN PATENT DOCUMENTS

WO  2022165245 A1  8/2022

OTHER PUBLICATIONS

Emrich et al. 2021 European Radiology Experimental 5:14 13 pages (Year: 2021).*

(Continued)

*Primary Examiner* — Keith M Raymond
*Assistant Examiner* — Patrick M Mehl
(74) *Attorney, Agent, or Firm* — Perkins Coie LLP

(57) ABSTRACT

A system is described for generating a revascularization score for a blockage of a coronary artery in a heart. The system accesses indications of viability of myocardial tissue in the heart, a blockage state of the blockage that includes a blockage location and a blockage amount, and the perfusion territory of the myocardial tissue. Based on the myocardial tissue state, blockage state, and perfusion territory, the system generates a revascularization score for the blockage. The system generates a graphic of the heart that illustrates coronary arteries, myocardial tissue state, blockage state, and the revascularization score. The system displays the graphic to provide a visual representation of the revascularization score for the blockage of the coronary artery.

30 Claims, 8 Drawing Sheets

(51) Int. Cl.
*A61B 6/03* (2006.01)
*A61B 6/46* (2024.01)
*G06T 7/00* (2017.01)
*G06T 7/11* (2017.01)
*G06T 7/62* (2017.01)
*G06T 17/20* (2006.01)

(52) U.S. Cl.
CPC ............ *A61B 6/507* (2013.01); *A61B 6/5217* (2013.01); *G06T 7/0012* (2013.01); *G06T 7/11* (2017.01); *G06T 7/62* (2017.01); *G06T 17/20* (2013.01); *G06T 2207/10081* (2013.01); *G06T 2207/20072* (2013.01); *G06T 2207/20081* (2013.01); *G06T 2207/20084* (2013.01); *G06T 2207/30048* (2013.01); *G06T 2207/30104* (2013.01)

(58) Field of Classification Search
CPC ........... G06T 7/0012; G06T 7/11; G06T 7/62; G06T 17/20; G06T 2207/10081; G06T 2207/20072; G06T 2207/20081; G06T 2207/20084; G06T 2207/30048; G06T 2207/30104
See application file for complete search history.

(56) References Cited

U.S. PATENT DOCUMENTS

| | | | |
|---|---|---|---|
| 11,896,432 | B2 | 2/2024 | Villongco et al. |
| 2004/0015081 | A1 | 1/2004 | Kramer et al. |
| 2010/0094274 | A1 | 4/2010 | Narayan et al. |
| 2012/0203124 | A1 | 8/2012 | Lim |
| 2014/0022250 | A1 | 1/2014 | Mansi et al. |
| 2015/0042646 | A1 | 2/2015 | Comaniciu et al. |
| 2015/0208936 | A1 | 7/2015 | Young et al. |
| 2016/0220137 | A1 | 8/2016 | Mahajan et al. |
| 2017/0220754 | A1 | 8/2017 | Harrah et al. |
| 2017/0232263 | A1 | 8/2017 | Narayan et al. |
| 2018/0028828 | A1 | 2/2018 | Cao et al. |
| 2019/0008462 | A1 | 1/2019 | Taylor |
| 2019/0059763 | A1 | 2/2019 | Shakur et al. |
| 2019/0082988 | A1 | 3/2019 | Datta et al. |
| 2019/0090769 | A1 | 3/2019 | Boleyn et al. |
| 2019/0333643 | A1 | 10/2019 | Narayan |
| 2020/0022649 | A1 | 1/2020 | Rodriguez |
| 2020/0175688 | A1 | 6/2020 | Krummen et al. |
| 2020/0205745 | A1* | 7/2020 | Khosousi ............... G16H 50/20 |
| 2020/0352462 | A1 | 11/2020 | Pedalty et al. |
| 2021/0272297 | A1 | 9/2021 | Chen et al. |
| 2021/0282731 | A1* | 9/2021 | Vaillant .................. A61B 6/032 |
| 2022/0008126 | A1 | 1/2022 | Tsoref et al. |
| 2022/0189636 | A1 | 6/2022 | Wagner et al. |
| 2022/0346856 | A1 | 11/2022 | Fedorov et al. |
| 2023/0172575 | A1* | 6/2023 | Kepka .................... G06V 10/26 382/130 |
| 2023/0230231 | A1* | 7/2023 | Tu ........................ G06V 10/774 382/130 |
| 2023/0260663 | A1* | 8/2023 | Ammirati ............... G06F 30/27 703/11 |
| 2023/0335289 | A1 | 10/2023 | Kuck |

OTHER PUBLICATIONS

Veelen et al. 2022 in Percutaneous Coronary Intervention for Chronic Total Occlusion Chap 4 p. 27-42 (Year: 2022).*
Dempsey 2020 PHD Thesis University of Western Ontario Canada 102 pages (Year: 2020).*
Zakkaroff et al. 2018 Computer Methods in Biomechanics and Biomedical Engineering Imaging Visualization 6:137-154 (Year: 2018).*
Cerci, Rodrigo et al., "Aligning Coronary Anatomy and Myocardial Perfusion Territories," Circ Cardiovasc Imaging, Sep. 2012, pp. 587-595.
Cleveland Clinic, "Hibernating Myocardium and Stunned Myocardium," retrieved May 30, 2023, 9 pages.
Garcia et al., "State of the Art: Imaging for Myocardial Viability," American Heart Association, Jul. 2020, 18 pages.
Kawel-Boehm et al., "Reference Ranges ("normal values") for cardiovascular magnetic resonance (CMR) in adults and children: 2020 update," Journal of Cardiovascular Magnetic Resonance, 63 pages.
Koyama et al., "Assessment of Reperfused Acute Myocardial Infartion with Two-Phase Contrast-enhanced Helical CT: Prediction of Left Ventricular Function and Wall Thickness," Radiology 2005, vol. 235, No. 3, pp. 804-811.
Li et al., "Prediction of 3D Cardiovascular hemodynamics before and after coronary artery bypass surgery via deep learning," Communications Biology, 2021, 13 pages.
Nakatani et al., "Quantitative Assessment of Coronary Artery Stenosis by Intravascular Doppler Catheter Technique," AHA Journals Circulation, vol. 85, No. 5, May 1992, pp. 1786-1791.
Panza et al., "Myocardial Viability and Long-Term Outcomes in Ischemic Cardiomyopthy," The New England Journal of Medicine, vol. 381, No. 8, Aug. 21, 2019, 17 pages.
Parikh et al., "Left and Codominant Coronary Artery Circulations Are Associated With Higher In-Hospital Mortality Among Patients Undergoing Percutaneous Coronary Intervention for Acute Coronary Syndromes: Report From the National Cardiovascular Database Cath Percutaneous Coronary Intervention (CathPCI) Registry," AHA Journals Circulation, Nov. 2012, pp. 775-882.
Ronneberger et al., "U-Net: Convolutional Networks for Biomedical Image Segmentation," Cornell University, May 18, 2015, arXiv:1505.04597v1, 8 pages.
Shapiro et al., "Assessing the available techniques for testing myocardial viability: what does the future hold?," Future Cardiology, Nov. 2012, 8(6), pp. 819-836.
Shehata et al., "Myocardial tissue tagging with cardiovasular magnetic resonance," Journal of Cardiovascular Magnetic Resonance, Dec. 21, 2009, 11, Article 55, 12 pages.
Velazquez et al., "Coronary-Artery Bypass Surgery in Patients with Ischemic Cardiomyopathy," The New England Journal of Medicine, vol. 374, No. 16, Apr. 21, 2016, pp. 1511-1520.
Yang et al., "3D Motion Modeling and Reconstruction of Left Ventricle Aall in Cardiac MRI," Funct Imaging Model Heart, Jun. 2017, 20 pages.
Yousefi-Banaem et al., "Prediction of myocardial infarction by assessing regional cardiac wall in CMR images through active mesh modeling," Computers in Biology and Medicine, Nov. 2016, pp. 56-64.
Han, C., et al. "Noninvasive reconstruction of the three-dimensional ventricular activation sequence during pacing and ventricular tachycardia in the rabbit heart." Conference Proceedings: Annual International Conference of the IEEE Engineering in Medicine and Biology Society,2011, pp. 1684-1687.
International Search Report and Written Opinion received in Application No. PCT/US23/75742, dated May 15, 2024, 21 pages.
Chen, et al., "Detection of left ventricular wall motion abnormalities from vol. rendering of 4DCT cardiac angiograms deep learning," Frontiers in Cardiovascular Medicine, published Jul. 28, 2022, 12 pages.
Bhattacharya, M et al. "Machine Learning Methods for Identifying Atrial Fibrillation Cases and Their Predictors in Patients With Hypertrophic Cardiomyopathy: The HCM-AF-Risk Model" 801-813. CJC Open vol. 3, Issue 6. Publication [online]. Jun. 2021 [Retrieved on May 9, 2024]; URL:[https://www.sciencedirect.com/science/article/pii/S2589790X21000317]; DOI: [https://doi.org/10.1016/j.cjco.2021.01.016]; entire document.
Vaswani, A., Shazeer, N., Parmar, N., Uszkoreit, J., Jones, L., Gomez, A.N., Kaiser, Ł. and Polosukhin, I., 2017. Attention is all you need. Advances in neural information processing systems, 30.
Gu, A. and Dao, T., 2023. Mamba: Linear-time sequence modeling with selective state spaces. arXiv preprint arXiv:2312.00752 (Mamba).
International Application No. PCT/US24/40474 entitled "Heart Wall Refinement of Arrhythmia Source Locations" and filed on Aug. 1, 2024.

(56) References Cited

OTHER PUBLICATIONS

Gómez-Barea, M., García-Sánchez, T. and Ivorra, A., 2022. A computational comparison of radiofrequency and pulsed field ablation in terms of lesion morphology in the cardiac chamber. Scientific reports, 12(1), p. 16144.
González-Suárez, A., Pérez, J.J., Irastorza, R.M., D'Avila, A. and Berjano, E., 2022. Computer modeling of radiofrequency cardiac ablation: 30 years of bioengineering research. Computer Methods and Programs in Biomedicine, 214, p. 106546.
Meckes, D., -Computational modeling of electric fields for lesion depth analysis. Heart Rhythm O2, 3(4), pp. 433-440.
Potse, M., Dubé, B., Richer, J., Vinet, A., & Gulrajani, R., 2006. A Comparison of Monodomain and Bidomain Reaction-Diffusion Models for Action Potential Propagation in the Human Heart. IEEE Transactions on Biomedical Engineering, 53, pp. 2425-2435.
Villongco, C.T., 2015. Patient-specific Computational Models of Dyssynchronous Heart Failure and Cardiac Resynchronization Therapy for Clinical Diagnosis and Decision Support. University of California, San Diego.
U.S. Appl. No. 63/550,020 titled "Cardiac Catheter Path Planning System" and filed on Feb. 5, 2024.
Non-Final Office Action received from the U.S. Patent and Trademark Office in U.S. Appl. No. 18/630,900, dated Aug. 27, 2024.
International Search Report and Written Opinion received for Application No. PCT/US24/23763, mailed on Sep. 19, 2024, 18 pages.
International Search Report and Written Opinion issued for PCT/US2024/040475; mailed on Sep. 9, 2024.
Emrich et al., "CMR for myocardial characterization in ischemic heart disease: state-of-the-art and future developments," European Radiology Experimental, 5:14; 13 pages, 2021.
Van Veelen et al., "Why, When and How to Assess Ischemia 4 and Viability in Patients with Chronic Total Occlusions," Percutaneous Coronary Intervention for Chronic Total Occlusion, Chapter 4, pp. 27-42, 2022.

* cited by examiner

TARGETING CORONARY REVASCULARIZATION BASED ON MYOCARDIAL VIABILITY

CROSS-REFERENCE TO RELATED APPLICATION

This application claims the benefit of U.S. Provisional Application No. 63/516,862 titled "TARGETING CORONARY REVASCULARIZATION BASED ON MYOCARDIAL VIABILITY" and filed on Aug. 1, 2023, which is hereby incorporated by reference in its entirety.

BACKGROUND

Coronary artery disease (CAD) is the most common type of heart disease. CAD may cause a myocardial infarction (MI) which may result in sudden cardiac death. According to the Centers for Disease Control and Prevention, among adults in the United States, the prevalence of CAD is approximately 5%, MIs is approximately 0.03% (~800,000) annually, and deaths from CAD is approximately 0.015% (~375,000) annually.

An MI typically occurs because of blood flowing though the coronary arteries is slowed or stopped, which adversely affects perfusion to the myocardial tissue. The blood flow may be slowed or stopped because of a blockage (e.g., calcification) in a coronary artery. Because of this adverse effect on blood flow, myocardial tissue is damaged or dies resulting in loss of contractility of myocardial tissue. Myocardial tissue may be categorized as being in a viable, diseased viable, or non-viable myocardial tissue state. As the terms are used in this document, viable refers to myocardial tissue that is functioning normally. Diseased viable refers to myocardial tissue that is functioning abnormally but can have its functioning improved if perfusion to it is improved. Non-viable refers to myocardial tissue that is not functioning and cannot have its functioning improved. Disease viable myocardial tissue may be categorized as stunned or hibernating. Stunned refers to myocardial tissue that is underperfused and not functioning properly but may have some functioning slowly restored if perfusion is sufficiently improved. Hibernating refers to myocardial tissue that is underperfused and downregulates its metabolic needs to survive but can have some of its functioning restored if perfusion is sufficiently improved.

To prevent further damage to the myocardial tissue, a coronary revascularization, such as a coronary artery bypass graft (CABG) or percutaneous coronary intervention (PCI) with or without a stent, may be performed. A coronary revascularization is often employed to increase blood flow to hibernating myocardial tissue but is typically not employed to increase blood flow to stunned myocardial tissue. The goal of these treatments is restoring blood flow through a coronary artery to improve perfusion to myocardial tissue to prevent further damage and restore function to diseased viable myocardial tissue. These treatments, however, can have serious complications such as infections, bleeding, stroke, and death. Moreover, a treatment may be effective if perfusion is maintained to viable myocardial tissue or improved to diseased viable myocardial tissue. However, treatment will not be effective if perfusion is improved only to non-viable myocardial tissue. If a treatment results in perfusion improving to only non-viable myocardial tissue, the treatment could have no benefit but has the risk of serious complications associated with revascularizations in general.

To assess whether a blockage is a candidate for revascularization, a cardiologist or cardiothoracic surgeon typically makes this assessment based on a visual inspection of myocardial tissue state derived from a heart scan. Various scanning techniques have been used to generate such scans but have problems that affect the ability to make accurate assessments. These scanning techniques include late gadolinium enhancement (LGE), positron emission tomography (PET), and nuclear medicine. The problems include poor resolution and complex protocols that are difficult to consistently perform correctly which may lead to inaccurate assessments.

To help improve the accuracy of assessing whether a blockage is a candidate for revascularization, it would be helpful to have a computer system to assist in determining whether revascularization would maintain perfusion to viable myocardial tissue and improve perfusion to diseased viable myocardial tissue.

DETAILED DESCRIPTION

Figure 1A:
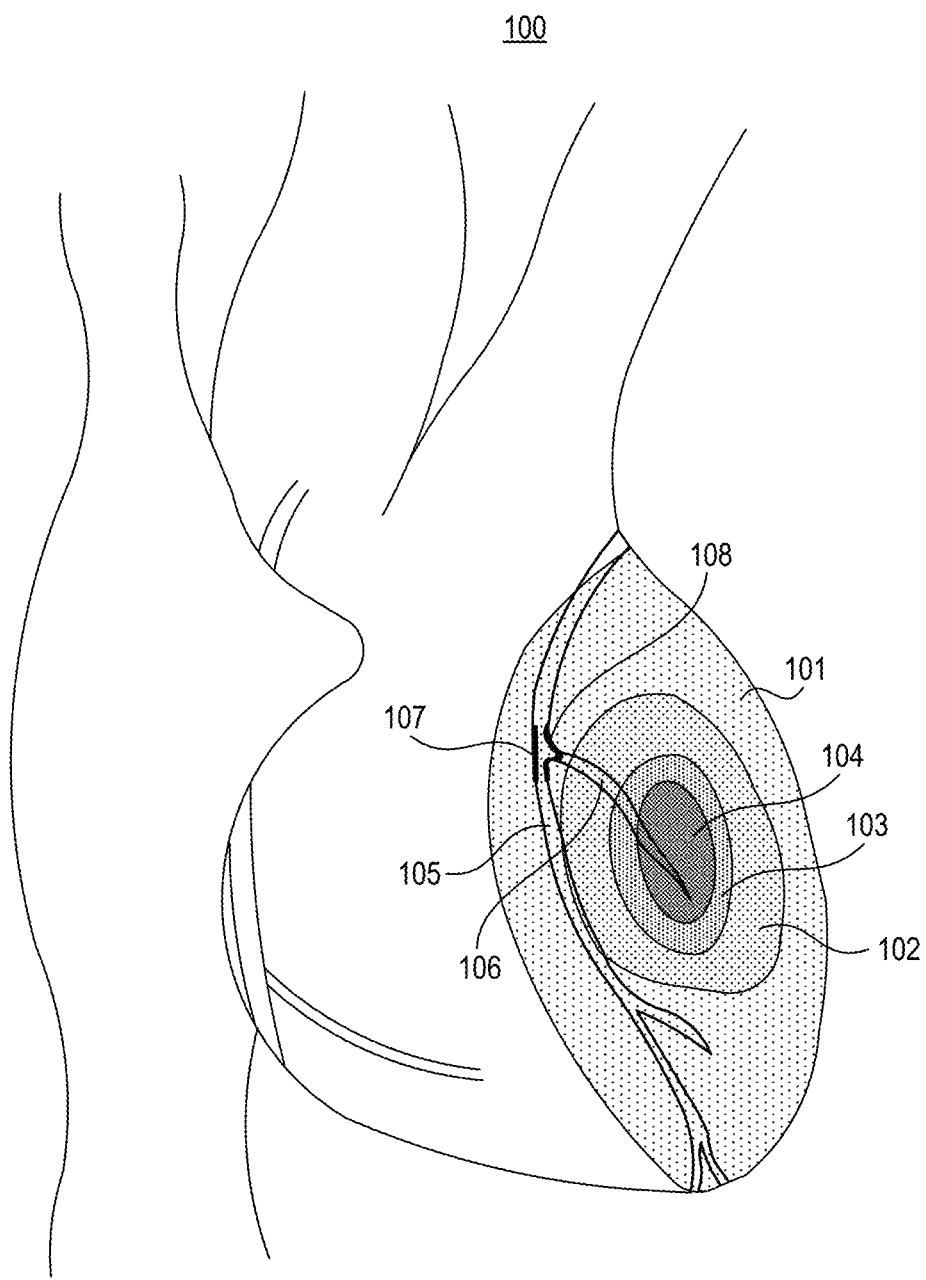
FIGS. 1A-1D provide 3D graphics that each illustrates coronary arteries, blockages and blockage state, and tissue state.

Systems and methods are described for evaluating potential revascularization targets for coronary revascularization in patients with CAD including those who have had an MI. In some embodiments, a targeting coronary revascularization (TCR) system generates a revascularization score for a coronary arterial blockage that indicates the likely benefit of a coronary revascularization based on that blockage. A blockage may be a complete blockage (e.g., chronic total occlusion) or a partial blockage (e.g., stenosis). The revascularization score may be determined based on blockage state (e.g., blockage amount and blockage location) and myocardial tissue state (also referred to as tissue state) of a perfusion territory associated with that blockage. The revascularization score may be used in conjunction with the risk associated with the revascularization to assess whether the benefit of the revascularization outweighs the risk. If so, the blockage may be considered to be a revascularization target. The revascularization score may also be used in assessing whether to employ PCI or CABG for the revascularization.

Myocardial tissue state indicates the viability of myocardial tissue that ranges from viable to non-viable. The viability is indicated by a viability score. A viability score may range from a minimum viability score to a maximum viability score such as continuous value (e.g., 0.0 to 1.0) or may be a classification such as viable, stunned, hibernating, and non-viable. Such classifications may be based on ranges of continuous values such as 0.0 to 2.9 for non-viable, 3.0 to 4.9 for hibernating, 5.0 to 6.9 for stunned, and 7.0 to 10.0 for viable. In the following, tissue state is primarily characterized by a viability score that is continuous with 0.0 representing non-viable myocardial tissue and 1.0 representing viable myocardial tissue.

The blockage state of a blockage indicates the blockage location and the blockage amount. The blockage location may indicate the coronary artery and the start and end of a blockage within that coronary artery. The blockage amount may be expressed as a blockage percentage 0% to 100% or a blockage fraction 0.0 to 1.0 that indicates the amount of narrowing with 0% or 0.0 representing no blockage and 100% or 1.0 representing complete blockage. The blockage amount may be derived from a flow percentage that indicates the percentage of the maximum blood flow that is expected to flow through the blockage location (assuming no blockage) with 0% indicating no blood flow and 100% indicating the maximum blood flow.

A perfusion territory of a coronary artery is the myocardial tissue that is normally perfused by that coronary artery. For example, the left anterior descending artery (LAD) perfuses the anterior wall of the left ventricle and the anterior part of the ventricular septum and may perfuse the apex of the heart. The left circumflex artery (LCx) perfuses the lateral and posterior walls of the left ventricle and may perfuse the left atrium. The right coronary artery (RCA) perfuses the right atrium, the right ventricle, and the inferior wall of the left ventricle and may perfuse the sinoatrial node and the atrioventricular node. The perfusion territory of a coronary artery may vary from person to person. For example, about 8% of the population is left dominant meaning the terminus of the LCx perfuses the posterior portion of the interventricular septum, and about 7% of the population is co-dominant meaning the RCA and LCx perfuse the posterior interventricular septum. (Parikh, N. I., Honeycutt, E. F., Roe, M. T., Neely, M., Rosenthal, E. J., Mittleman, M. A., Carrozza Jr, J. P. and Ho, K. K., 2012. Left and codominant coronary artery circulations are associated with higher in-hospital mortality among patients undergoing percutaneous coronary intervention for acute coronary syndromes: report From the National Cardiovascular Database Cath Percutaneous Coronary Intervention (CathPCI) Registry. Circulation: Cardiovascular Quality and Outcomes, 5(6), pp. 775-782.)

The TCR system may employ various machine learning (ML) models, non-ML algorithms, or combinations of both, to generate a revascularization score. The TCR system may employ a TCR ML model that inputs a feature vector that includes one or more features derived from cardiac images of a patient and outputs a revascularization score for a blockage. (A feature of an image may be the image itself.) The TCR ML model may comprise various ML sub-models such as a wall characteristics ML model, a tissue state ML model, and a scoring ML model. The wall characteristics and tissue state may be indicated using a three-dimensional (3D) mesh. (The various 3D meshes that are described may be based on the cardiac geometry of a patient.) The 3D mesh includes vertices representing locations within the heart wall that are associated with various cardiac characteristics such as tissue state. The cardiac characteristics also may be associated with voxels within the 3D mesh. A technique for generating a 3D mesh from a 3D image is described in Int. Pub. No. WO 2023/168017 titled "Overall Ablation Workflow System" and published on Sep. 7, 2023, which is hereby incorporated by reference.

A wall characteristics ML model determines heart wall characteristics such as wall thickness, wall motion, and/or wall strain at various locations within the heart wall. The wall characteristics ML model inputs a feature vector with features derived from a four-dimensional (4D) cardiac image (which may be segmented) of a patient and outputs a wall characteristics 3D mesh. A wall characteristics 3D mesh has wall characteristics associated with vertices or voxels within the heart wall. A 4D image comprises a sequence of 3D images collected at time intervals that each comprise 2D images (slices). A computed tomography (CT) scan is a 4D image. A 4D mesh is a sequence of 3D meshes that may be generated based on a 4D image.

A tissue state ML model determines the tissue state of myocardial tissue. The tissue state ML model inputs a wall characteristics 4D mesh and outputs a tissue state 3D mesh. The tissue state ML model generates a viability score indicating tissue state that may be a continuous value (e.g., 0.0 to 1.0) or is a classification (e.g., hibernating). A tissue state 3D mesh has viability score associated with vertices or voxels.

The scoring ML model generates a revascularization score for a blockage that indicates the likely benefit of revascularization based on that blockage. The scoring ML model inputs the blockage state and the perfusion territory of a blockage and a tissue state 3D mesh and outputs a revascularization score for the blockage. The perfusion territory of a blockage encompasses the territory perfused by normal blood flow (with no blockage) through the blockage location. The perfusion territory of a blockage includes the territory perfused by normal blood flow through the downstream portion of the coronary artery. The perfusion territory may be represented by a perfusion 3D mesh subdivided into voxels. Each voxel is associated with a perfusion factor that indicates how much of its perfusion would be provided by normal blood flow through the blockage location. The perfusion factor may be expressed, for example, as a perfusion percentage or perfusion fraction. The perfusion territory of a blockage is primarily based on the downstream portion but may extend upstream to some extent. If a blockage percentage is less than a revascularization blockage threshold (e.g., 40%), the blockage would typically not be considered a revascularization target irrespective of the tissue state within its perfusion territory. In such a case, the TCR system may set the revascularization score for such a blockage to 0 or may only consider a blockage percentage above the threshold blockage percentage to represent a blockage.

A wall characteristics ML model may be trained using training data such as 4D images derived from electronic health records (EHRs) and wall characteristics 3D meshes derived from the 4D images. A training data set includes a 4D image (or 4D mesh generated from the 4D image) labeled with a wall characteristics 3D mesh. The wall characteristics for the training data may be determined by employing a wall characteristics algorithm (non-ML) such as the one described below or may be manually demarcated on the 4D images. An ML model (e.g., wall characteristics ML model) and a corresponding algorithm (e.g., wall characteristics algorithm) for performing a function (e.g., determine wall characteristics) are referred to as techniques for that function.

A wall characteristics ML model may also be trained using training data derived from simulations of electrical activity and motion of a heart. Such a wall characteristics ML model may input 3D meshes (i.e., a 4D mesh) representing changes in cardiac geometry at simulation intervals of a cardiac cycle or may input a 4D image derived from the 3D meshes. To generate such a 4D image, the TCR system may, for each 3D mesh, employ ray tracing through the 3D mesh to generate slices of a 3D image of the 4D image.

Alternatively, the TCR system may divide a 3D mesh into voxels and generate slices of the 3D image based on the voxels. Each simulation assumes a different heart configuration such as cardiac geometry, arrythmia source location, source type (e.g., focal or reentrant), tissue states, electrical characteristics (e.g., action potential and conduction velocity), and so on. Simulations of electrical activity of a heart is described in U.S. Pat. No. 10,319,144 titled "Computational Localization of Fibrillation Sources" and issued on Jun. 11, 2019 and in Villongco, C.T., 2015. Patient-specific Computational Models of Dyssynchronous Heart Failure and Cardiac Resynchronization Therapy for Clinical Diagnosis and Decision Support. University of California, San Diego, which are hereby incorporated by reference. Wall characteristics based on the 3D meshes of a simulation may be determined based on the locations of the vertices of the 3D meshes using a wall characteristics algorithm. A training data set of the training data may include 3D meshes (e.g., representing maximum contraction and maximum expansion) labeled with a wall characteristics 3D mesh.

A wall characteristics algorithm (non-ML) may determine wall characteristics based on analysis of vertices of 3D meshes. Such a wall characteristics algorithm determines wall characteristics based on the locations associated with the vertices. The TCR system may associate wall thickness with endocardial vertices of a 3D mesh. The wall thickness of an endocardial vertex may also be based on the distance between that endocardial vertex and the closest epicardial vertex or the closest epicardial vertex in a specified direction (e.g., xy-plane or radially from a point within a chamber) at maximum contraction of a cardiac chamber. The search for the closest epicardial vertex may employ a spatial decomposition tree (SD-tree). An SD-tree organizes data by recursively subdividing the space into regions and storing information about these subdivisions. Each node in the SD-tree represents a region of space, and the leaves correspond to locations associated with vertices of the endocardium and epicardium. Another algorithm for determining wall thickness is described in Augusto, J. B., Davies, R. H., Bhuva, A. N., Knott, K. D., Seraphim, A., Alfarih, M., Lau, C., Hughes, R. K., Lopes, L. R., Shiwani, H. and Treibel, T. A., 2021. Diagnosis and risk stratification in hypertrophic cardiomyopathy using machine learning wall thickness measurement: a comparison with human test-retest performance. The Lancet Digital Health, 3(1), pp.e20-e28, which is hereby incorporated by reference.

The wall characteristics algorithm may calculate wall motion associated with endocardial vertices. The wall motion of an endocardial vertex may be based on the distance between that endocardial vertex at maximum contraction and maximum expansion. Various techniques may be employed to determine wall motion based on analysis of 3D meshes representing the cardiac geometry over time. Such techniques are described in Yang, D., Wu, P., Tan, C., Pohl, K. M., Axel, L. and Metaxas, D., 2017. 3D motion modeling and reconstruction of left ventricle wall in cardiac MRI. In Functional Imaging and Modelling of the Heart: 9th International Conference, FIMH 2017, Toronto, ON, Canada, Jun. 11-13, 2017, Proceedings 9 (pp. 481-492). Springer International Publishing and in Yousefi-Banaem, H., Asiaei, S. and Sanei, H., 2017. Prediction of myocardial infarction by assessing regional cardiac wall in CMR images through active mesh modeling. Computers in Biology and Medicine, 80, pp. 56-64, which are hereby incorporated by reference.

The wall characteristics algorithm may calculate wall strain for pairs of locations within the heart wall. The wall characteristics algorithm may calculate wall strain for every vertex or only for vertices corresponding to certain locations such as the endocardium, myocardial midline, and epicardium. The wall strain for a pair of vertices may be based on the difference in their locations at the maximum contraction and maximum expansion divided by the difference in their locations at maximum expansion (or at other stages of the cardiac cycle other than maximum contraction and maximum expansion). Various types of wall strain measurements can be made such as longitudinal strain, radial strain, and circumferential strain. The longitudinal strain is based on difference in length of the heart over time. The longitudinal strain may be calculated by calculating the difference in the length of the ventricles at maximum expansion and at maximum contraction and dividing the difference by the length at maximum expansion. Radial strain is based on difference in heart wall thickness over time. The radial strain may be calculated by calculating the difference in maximum expansion wall thickness and maximum contraction wall thickness measured in the x-y plane and dividing the difference by the maximum expansion wall thickness. The x-y plane is a horizontal plane. Circumferential strain is based on changes in the circumference of the heart over time. The circumferential strain may be calculated based on calculating the difference in maximum expansion circumference and maximum contraction circumference measured in the x-y plane and dividing that difference by the maximum expansion circumference. In addition, a strain rate can be calculated for various periods within a cardiac cycle such as for a ventricular vertex based on maximum contraction and expansion of an atrium. The strain rate is the derivative of strain with respect to time. The derivative is calculated based on calculating a difference in a certain at two points in the cardiac cycle and dividing that difference by the difference in time of those two points. The strain rate is a type of wall characteristics that may be generated by the wall characteristics ML model or the wall characteristics algorithm and used to determine tissue state. The wall characteristics can be based on various other measurements such as Cauchy strain (1D), stretch ratio, displacement field (3D), and deformation gradient. (See, Lubliner, J., 2008. Plasticity theory. Courier Corporation.)

A tissue state ML model determines the tissue state within the heart wall based on wall characteristics. The tissue state ML model inputs a wall characteristics 3D mesh and outputs a tissue state 3D mesh or voxels within the 3D mesh. The training data for the tissue state ML model may be derived from 4D images (e.g., CT scan) of EHRs with a 3D image of a 4D image demarcated with tissue state. To generate training data sets, a wall characteristics algorithm may be used to generate a wall characteristics 3D mesh for each 4D image. A tissue state 3D mesh corresponding to a wall characteristics 3D mesh may be generated for each 4D image from a demarcated 3D image. To generate a tissue state 3D mesh, the tissue state for a vertex is derived from the wall characteristics 3D mesh using, for example, a tissue state algorithm (non-ML) as described below. A training data set of the training data includes a wall characteristics 3D mesh labeled with a tissue state 3D mesh. The tissue state ML model may alternatively input a 4D image and output a tissue state 3D mesh. In such a case, a training data set includes a 4D image labeled with a tissue state 3D mesh.

A tissue state algorithm (non-ML) generates a tissue state 3D mesh based on analysis of a wall characteristics 3D mesh. The tissue state algorithm may apply an equation based on the wall characteristics to generate a viability score for tissue. The viability score associated with a vertex is the weighted sum of variables set to the values of wall characteristics for that vertex and mapped to be within a range of 0 and 100 percent or 0.0 to 1.0 indicating viability. The weights may be determined based on analysis of 4D images of EHRs demarcated with tissue state. The wall characteristics ML model may be employed to determine the wall characteristics of the 4D images. The TCR system may employ an optimization process that determines weights (e.g., for strain, strain rate, motion, and/or thickness) that tend to minimize the incorrect determination of tissue state. Alternatively, the TCR system may, for each wall characteristic, generate a histogram of the values for that wall characteristic derived from 4D images of EHRs. For example, a histogram for strain indicates, for each strain value, the number of voxels of the 4D images that correspond to that strain value. Strain thresholds may be specified to indicate ranges of strain values corresponding to viable, stunned, hibernating, and non-viable. The ranges may be manually specified or may be determined using an optimization process that tends to minimize incorrect determinations. Given the ranges, the TCR system may determine weights for each wall characteristic as described above. As another example, the tissue state algorithm may employ a distribution (e.g., Gaussian) derived from EHRs to determine tissue state. With such a distribution, the cutoff points for tissue state may be one standard deviation of the mean for viable tissue, one to two standard deviations for likely viable, and more than two standard deviations for non-viable. The cutoff points may be specified manually or determined algorithmically based on tissue state of the EHRs. A technique for determining tissue state based on an MRI scan are described in Shehata, M. L., Cheng, S., Osman, N. F., Bluemke, D. A. and Lima, J. A., 2009. Myocardial tissue tagging with cardiovascular magnetic resonance. Journal of Cardiovascular Magnetic Resonance, 11, p.55, which is hereby incorporated by reference. Several techniques for determining tissue state are described in U.S. Pat. No. 11,896,432 titled "Machine Learning for Identifying Characteristics of a Reentrant Circuit" and issued on Feb. 13, 2024, which is hereby incorporated by reference. The tissue state algorithm (and tissue state ML model) may also factor in other data (that is other than wall characteristics) from the EHRs. For example, this data may include a patient's age, source location of an arrhythmia, blockage state, blood pressure, smoking history, diabetes, and so on. Examples of such data are described in Kawel-Boehm, N., Hetzel, S. J., Ambale-Venkatesh, B., Captur, G., Francois, C. J., Jerosch-Herold, M., Salerno, M., Teague, S. D., Valsangiacomo-Buechel, E., Van der Geest, R. J. and Bluemke, D. A., 2020. Reference ranges ("normal values") for cardiovascular magnetic resonance (CMR) in adults and children: 2020 update. Journal of cardiovascular magnetic resonance, 22(1), p.87, which is hereby incorporated by reference. The source location may be identified as described in U.S. Pat. No. 10,860,754 titled "Calibration of Simulated Cardiograms" and issued on Dec. 8, 2020, which is hereby incorporated by reference.

The TCR system may employ various ML model architectures for processing the various 3D meshes. In some embodiments, the TCR system may employ a Graph Neural Network (GNN). A GNN is designed to operate on graph data based on convolutions over neighborhoods of nodes of the graph data. A 3D mesh can be viewed as a graph where vertices are nodes and edges are connections between these nodes. GNNs operate by passing messages between nodes (vertices) and aggregating information from neighbors. Weights that are learned for vertex-level features depend on both the individual properties of vertices and their relations to neighbors. (See, Gori, M., Monfardini, G. and Scarselli, F., 2005 July. A new model for learning in graph domains. In Proceedings. 2005 IEEE International Joint Conference on Neural Networks, 2005. (Vol. 2, pp. 729-734). IEEE, which is hereby incorporated by reference.) In some embodiments, different types of GNNs may be employed such as a Graph Attention Network, which implements an attention mechanism, or a Graph Convolutional Network, which implements convolutions. The training data may include a 3D mesh with each vertex has features and a label. When training a GNN, nodes send information to neighboring nodes based on a loss function to learn the weights for features of the nodes. After the GNN is trained, a 3D mesh (e.g., wall strain 3D mesh or tissue state 3D mesh) can be input to the GNN to generate a label for each node based on features of nodes of the 3D mesh.

A GNN processes a graph G=(V,E) that consists of nodes (vertices) V and edges E that connect pairs of nodes. Nodes and edges can have features that describe characteristics such as wall thickness and tissue state. GNNs typically operate through a mechanism known as message passing or neighborhood aggregation. In each layer of a GNN, nodes aggregate information (messages) from their neighbors. This aggregation helps nodes to learn about their local graph structure. Nodes can update their features by combining their own features with aggregated messages from their neighbors, often using neural networks. Edges can also have features and play a role in how messages are passed and aggregated. A GNN layer may perform the following processing:

$$av(l+1)=\text{AGGREGATE}(l)(\{hu(l):u \in N(v)\})$$

$$hv(l+1)=\text{COMBINE}(l)(hv(l),av(l+1))$$

where hv(l) is the feature vector of node v at layer l, N(v) represents the neighbors of v, and av (l+1) is the aggregated information. Gradient descent may be employed to optimize the parameters of the aggregate and combine functions.

Other ML models that may be employed such as a Mesh Convolutional Neural Network (Mesh CNN) or Point Cloud Network (PCN). A Mesh CNN employs convolutions that account for the irregular structure of a 3D mesh. A Mesh CNN applies filters to the surfaces defined by the 3D mesh. A PCN treats the vertices of a 3D mesh as points. A PCN may process each vertex individually to extract features and apply a symmetric function to ensure permutation invariance among points. Tools provided by PyTorch may be employed to implement and train various ML models. PyTorch is an open-source deep learning framework developed by Facebook's AI Research Lab. (www.pytorch.org.)

The TCR system may employ a predefined or a patient-specific specification of perfusion territories. Predefined perfusion territories are representative of the perfusion territories found in a population of patients (e.g., with typical coronary arterial trees). There are various well-known descriptions of predefined perfusion territories. (See, Cerci, R. J., Arbab-Zadeh, A., George, R. T., Miller, J. M., Vavere, A. L., Mehra, V., Yoneyama, K., Texter, J., Foster, C., Guo, W. and Cox, C., 2012. Aligning coronary anatomy and myocardial perfusion territories: an algorithm for the CORE320 multicenter study. Circulation: Cardiovascular Imaging, 5(5), pp. 587-595, which is hereby incorporated by reference.) A patient-specific perfusion territory of a coronary artery can be determined in various ways. One technique for determining patient-specific perfusion territories is to identify the coronary arterial tree (or portion of it) of a patient and the diameters at various locations along the paths. The paths and diameters can be determined in various ways such as based on analysis of angiograms. If the path of a portion of an arterial tree cannot be determined (e.g., because of blockage of blood flow to that portion), the TCR system may derive that path from a predefined arterial tree that is representative of the arterial trees found in a population of patients. An arterial tree ML model may input an angiogram and output an indication of the paths and diameters. The training data may be derived from EHRs having angiograms labeled with an indication of the paths and diameters. Various ML models may be employed to implement the arterial tree ML model. For example, a convolutional neural network (e.g., U-net) may input an angiogram (e.g., X-ray image) and output the coronary arterial tree represented by the image along with the arterial diameters.

The paths and diameters may also be determined using a non-ML algorithm based on direct analysis of the angiograms to trace the flow of dye based on grayscale variations. An arterial tree may be represented as a 3D mesh of the epicardium of a heart with vertices corresponding to locations on the epicardium. A vertex that corresponds to a location along an artery may indicate the name of that artery. An arterial tree may alternatively be represented by, for each artery, a list of arterial locations, which may be in the reference frame of a standard heart model.

Given the paths and diameters, the perfusion territory for a location along an artery can be determined based on its diameter and the diameters of and distances to locations along nearby arteries. The perfusion territory may be defined as the ratio of the diameters to the distance between the locations. For example, if the distance between the locations is 1 cm and the diameters are 6 mm and 4 mm, then the perfusion territory for the 6 mm diameter artery encompasses 60% of the distance. Since there is actually overlap in perfusion territories, a perfusion territory may have a perfusion percentage (or more generally a perfusion factor) associated with voxels within perfusion territory. The percentage indicates the percentage of perfusion (decay in perfusion) to a territory location that is provided by an artery which decreases with distance from the artery. If there is a blockage in a coronary artery, the path and diameter downstream cannot be determined from an angiogram. In such a case, a standard perfusion territory may be employed for the downstream portion.

The flow percentage of a blockage state may be determined from an angiogram based on analysis of coronary artery blood flow through the blockage. The blockage percentage may be determined from cardiac gated CT scan based on analysis of calcification of the blockage or be derived from the flow percentage. The flow percentage and blockage percentage may also be manually determined and input to the TCR system. Various ML models may also be employed to determine flow percentage. (See, Li, G., Wang, H., Zhang, M., Tupin, S., Qiao, A., Liu, Y., Ohta, M. and Anzai, H., 2021. Prediction of 3D Cardiovascular hemodynamics before and after coronary artery bypass surgery via deep learning. Communications biology, 4(1), p.99, which is hereby incorporated by reference.)

The scoring ML model generates a revascularization score for a blockage based on its blockage state and based on the tissue states (represented as a viability score) and the perfusion fractions in its perfusion territory. The tissue states and perfusion fractions are associated with voxels that subdivide the perfusion territory of the blockage. The depth of a perfusion territory extends from the epicardium to the endocardium. The scoring ML model inputs a feature vector representing a blockage and outputs a revascularization score. The feature vector for a blockage has features representing its blockage state and, for each voxel in its perfusion territory, a viability score and perfusion fraction. The training data for the scoring ML model is composed of, for each blockage, a training data set that includes a feature vector and a label. The revascularization scores for the training data may be calculated based on the non-ML scoring algorithm described below. The scoring ML model may be implemented using a GNN or a PCN with the voxels represented as vertices of a graph or points of a point cloud.

A revascularization score for a blockage may range 0.0 to 1.0 with 0.0 representing that revascularization will likely have very little if any benefit and 1.0 representing that revascularization will likely have significant benefit. For example, if a perfusion territory has only non-viable tissue (viability scores near 0.0), the revascularization score would be low because a revascularization would have very little benefit. If a perfusion territory has only a small amount of viable and diseased viable tissue (e.g., viability scores >0.5), and the blockage fraction is around 0.6, the vascularization score would be somewhat higher. If a perfusion territory has only viable and diseased viable tissue and is large and the blockage fraction is high, the revascularization score would be much higher.

A scoring algorithm may be implemented using various techniques. One technique assumes that the largest possible revascularization score of 1.0 is associated with a total blockage that has the largest perfusion territory with every voxel having a viability score of 1.0 and a perfusion fraction is 1.0. For example, the perfusion territory for a blockage at the beginning of the left anterior descending (LAD) artery may be largest. This technique, for each voxel in the perfusion territory, calculates the product of the perfusion fraction and viability score for that voxel. If a voxel has a perfusion fraction of 0.25 and the viability score is 0.5, then the benefit of revascularization to that voxel assuming a blockage fraction of 1.0 would be 0.125 (i.e., 0.25*0.5*1.0). However, if the perfusion fraction is 0.5, the benefit would 0.25 (i.e., 0.5*0.5*1.0). The technique sums the products of all the voxels and divides by the blockage fraction to give an unnormalized revascularization score. For example, if a small and a large perfusion territory for a blockage have a viability score of 0.5 and perfusion fraction of 0.5 for every voxel and the blockage fractions are the same, then the large perfusion territory would have a larger unnormalized revascularization score. This score is considered to be unnormalized because it can range from the zero to the number of voxels in the largest perfusion territory which is not in the range of 0.0 to 1.0 of a revascularization score. The revascularization score may be generated by dividing the unnormalized revascularization score by the maximum possible unnormalized revascularization score. The maximum possible revascularization score with this technique can be represented by the number of voxels in the largest perfusion territory because each voxel has a value of 1.0 for the product of the perfusion fraction of 1.0 times the viability score of 1.0. The unnormalized revascularization score (UnReVas) and the revascularization score (ReVas) can be represented by the following equations:

$$UnReVas = \sum (\text{perfusion} * \text{viability}) * \text{blockage}$$

$$Revas = \frac{UnRevas}{\max \cdot UnRevas}$$

where perfusion is perfusion fraction, viability is viability score, blockage is blockage fraction, and max. UnRevas is the maximum unnormalized revascularization score.

Another technique for generating a revascularization score is to associate weights with the variables of the equations or more generally employ weight functions. For example, a blockage weight function for the blockage may be based on the assumption that there is a non-linear relationship between blockage fraction and benefit of revascularization. For example, revascularization of blockages with blockage fractions of 1.0 and 0.9 may have essentially the same benefit. To account for this, the revascularization score may be based on a blockage weight function that is the square root or cube root of the blockage fraction. As another example, a viability weight function for the viability score may be based on the assumption that there is a non-linear relationship between viability score and the benefit of revascularization. For example, tissue with a viability score of 1.0 is very healthy even though there is a blockage. To account for this, the revascularization score may be based on a viability weight function that effectively reduces viability scores near 1.0 such as a sigmoid-type function where the weight rises from the viability score of 1.0 and levels off at 0.9.

The TCR system may provide revascularization scores for multiple blockages in a coronary artery which may be referred to as an upstream and a downstream blockage. The TCR system may calculate a revascularization score for each individually assuming the other is not revascularized. For example, a downstream blockage could have a high revascularization score if the upstream blockage has a low blockage percentage, and the downstream blockage has a high blockage percentage and a large perfusion territory that is mostly viable and diseased viable. In such a case, a medical provider may decide to treat such a downstream blockage with a stent rather than a CABG. To factor in the effect of the upstream blockage, the blockage state may indicate a pre-revascularization and a post-revascularization blood flow percentage. The post-revascularization blood flow percentage is the pre-vascularization blood flow percentage of the upstream blockage (assuming no branches in between them).

The TCR system may generate a combined revascularization score, assuming that each is revascularized. The combined revascularization score may be generated based on the upstream and downstream revascularization scores such as an average of the revascularization score. The combined revascularization may also be the revascularization score of the upstream blockage assuming no downstream blockage.

After identifying the myocardial tissue state, the TCR system generates a three-dimensional (3D) graphic based on a 3D mesh that includes an indication of a tissue state and an indication of a viability score for each voxel within the 3D mesh, an indication of the coronary arteries, and for each blockage, an indication of the blockage state, the perfusion territory, and a revascularization score. The tissue state may be indicated using colors (e.g., blue viable and red nonviable), grayscale or color gradients, cross-hatchings, and so on. The perfusion territory of the blockage (and adjacent perfusion territories) may be indicated by their boundaries (e.g., where perfusion drops off to below 10%). The perfusion percentages may be indicated, for example, by a red color gradient. The revascularization score may be indicated by a numerical value or color gradient, for example, from light green to dark green. When a cursor is moved over an area such as a perfusion territory, the TCR system may display a pop-up window with information about that perfusion territory such as percentage of viable, disease viable, and non-viable tissue or perfusion percentage. The TCR system may also employ checkboxes to select the type of information to be displayed on the graphic such as perfusion territory, perfusion percentage, and blockage state. The TCR system also may also provide the options of display slices of the heart so that information at various depth within the myocardium can be viewed and assessed. The TCR system allows a user to rotate the graphic of the heart through any orientation, that is, any spherical angle (e.g., azimuthal angle and polar angle). By rotating the graphic, the user may better understand the full extent of perfusion territories and their relations of various coronary arteries.

Figure 1B:
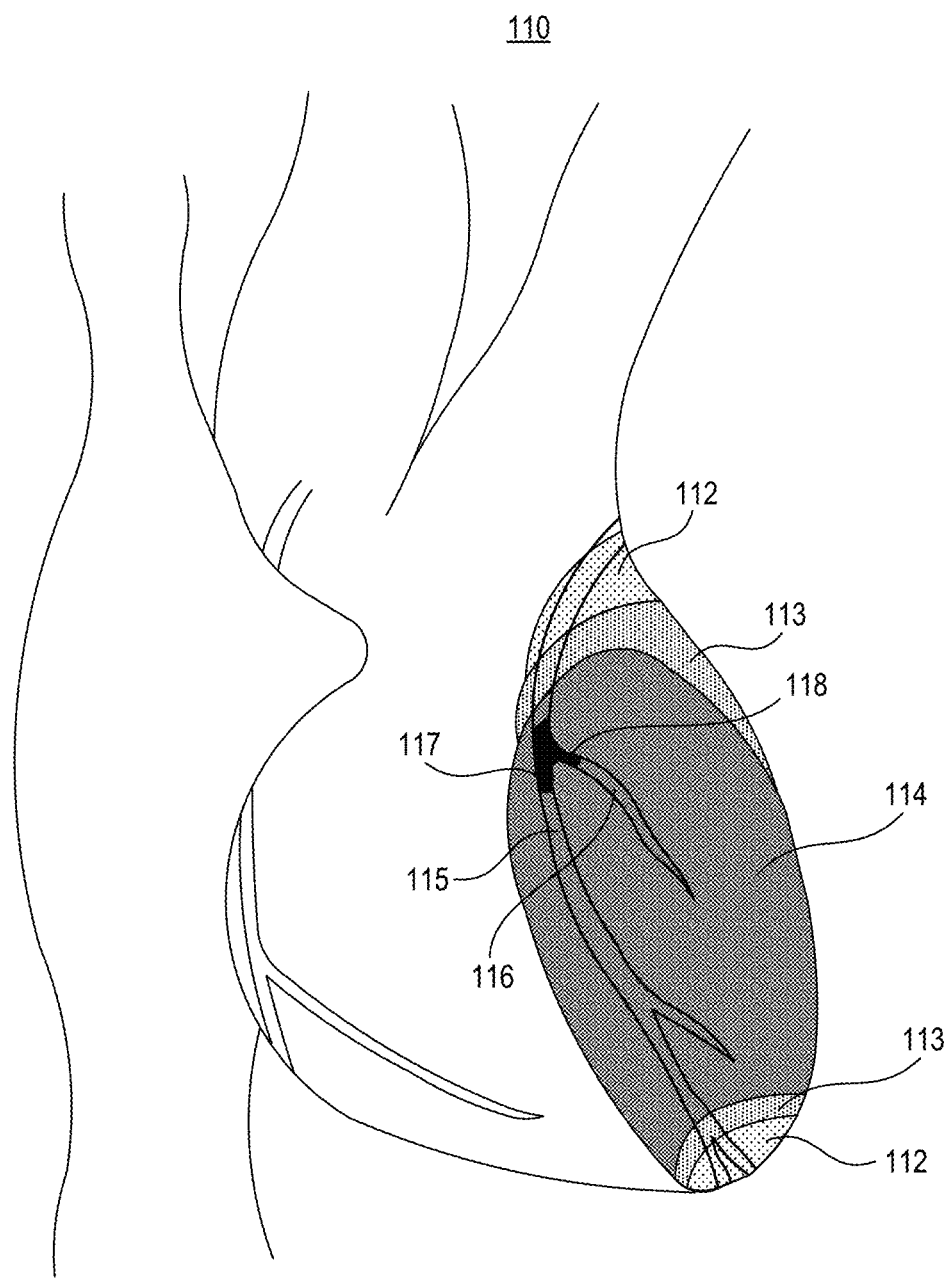
Figure 1C:
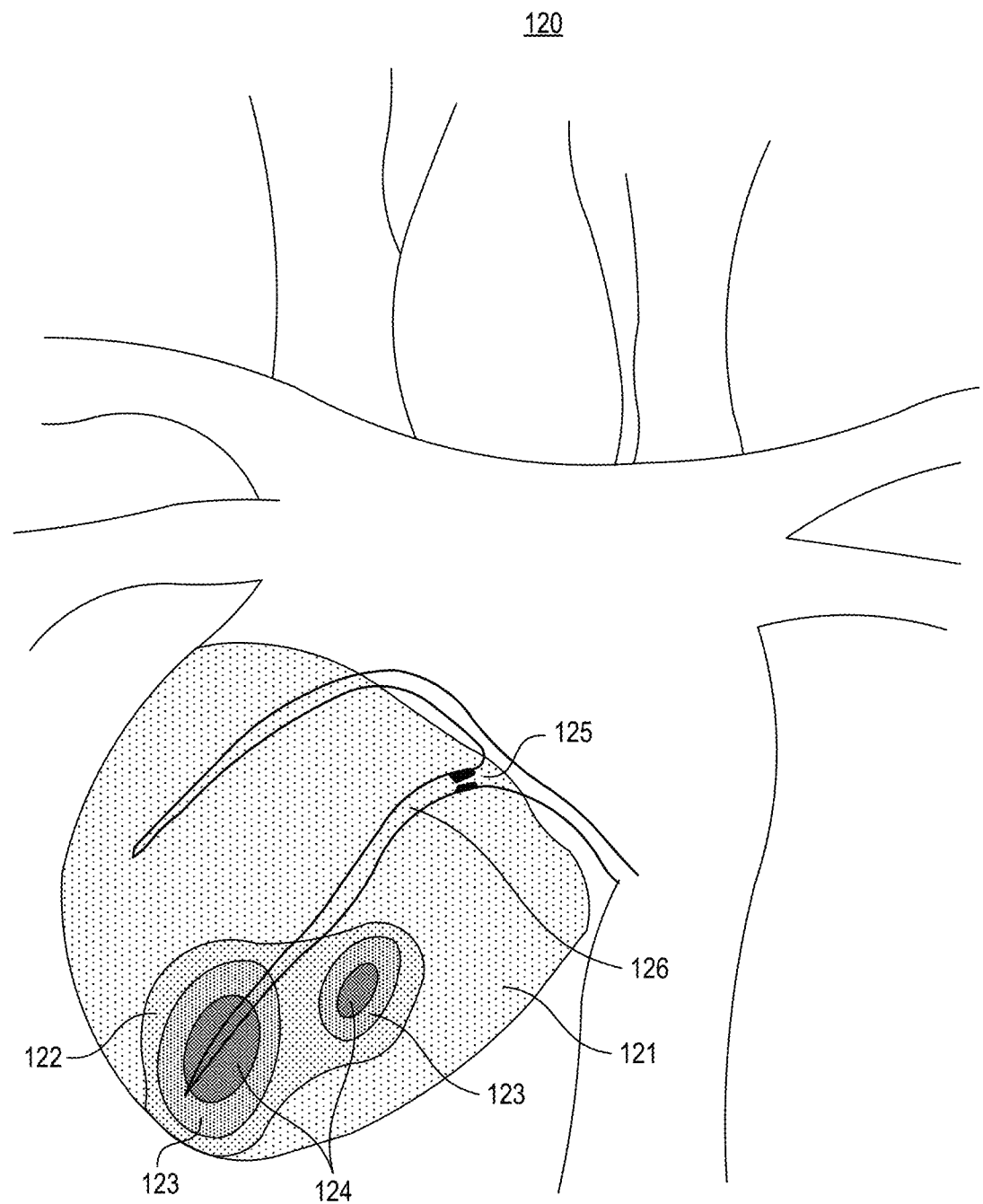
Figure 1D:
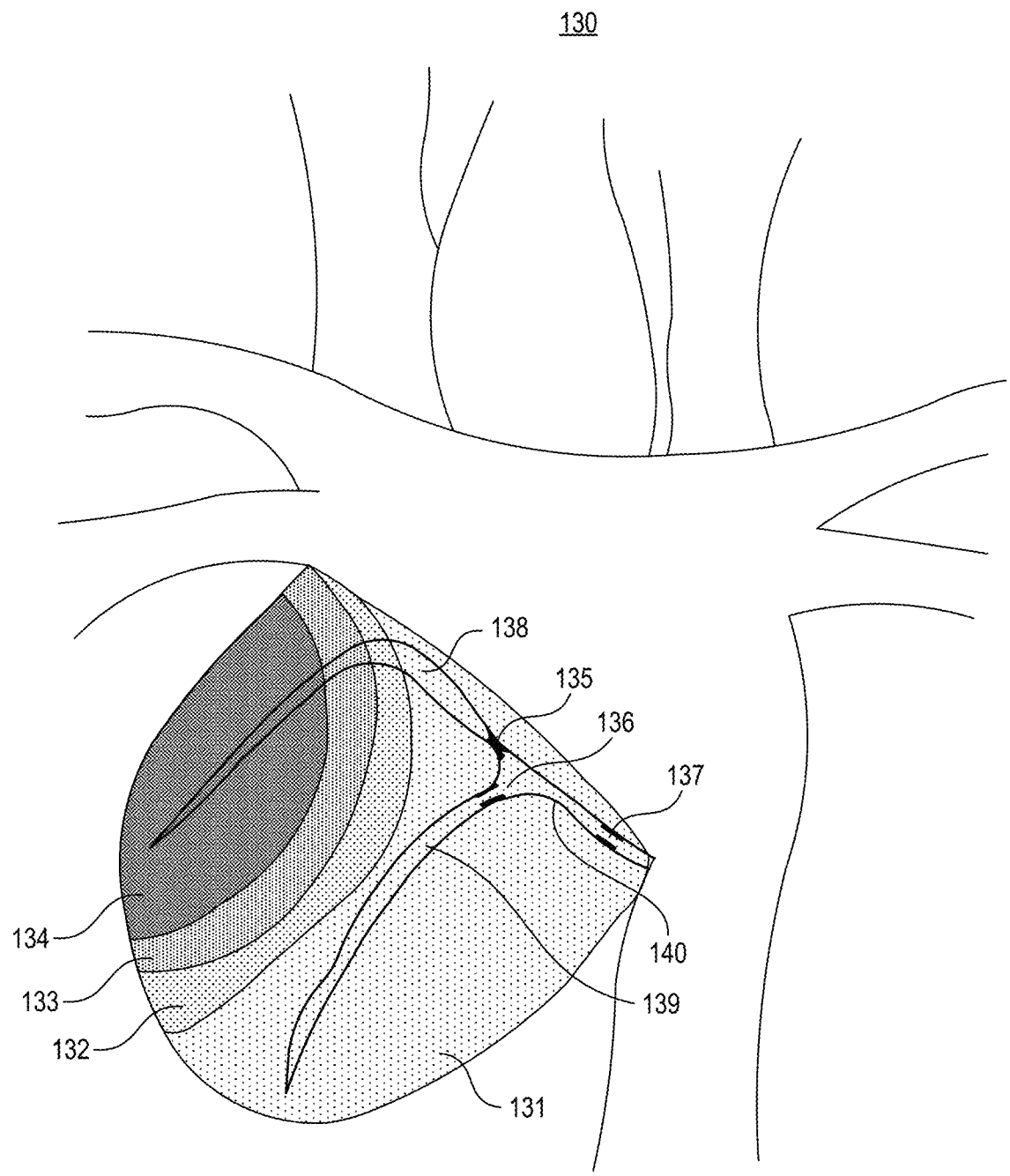

FIGS. 1A-1D provide 3D graphics that each illustrates coronary arteries, blockages and blockage state, and tissue state. In FIG. 1A, the 3D graphic 100 illustrates the anterior wall. The blockage 107 of the left anterior descending (LAD) coronary artery 105 is 80%, and the blockage 108 of the diagonal branch 106 is 95%. The combined perfusion territory for the blockage is illustrated by the lined area. Areas 101, 102, 103, and 104 of the combined perfusion territory correspond to the tissue states of viable, stunned, hibernating, and non-viable, respectively. Because there is significant diseased tissue (e.g., hibernating) in the perfusion territory of the diagonal branch blockage and significant viable cardiac tissue in the perfusion territory of the LAD coronary artery blockage, the TCR system may provide a high revascularization score for both blockages. In FIG. 1B, the 3D graphic 110 also illustrates the anterior wall. The blockage 117 of the left anterior descending (LAD) coronary artery 115 is a chronic total blockage (CTO), and the blockage 118 of the diagonal branch 116 is also a CTO. The combined perfusion territory for the blockage is illustrated by the lined area. Areas 112, 113, and 114 of the combined perfusion territory correspond to the tissue states of stunned, hibernating, and non-viable, respectively. Since the tissue in the perfusion territory is non-viable, the TCR system may provide a low revascularization score for each blockage. In FIG. 1C, the 3D graphic 120 illustrates the inferior wall. The blockage 125 of the posterior descending artery (PDA) 126 is 80%. Areas 121, 122, 123, and 124 of the combined perfusion territory correspond to the tissue states of viable, stunned, hibernating, and non-viable, respectively. Since the vast majority of tissue in the perfusion territory is viable or diseased viable, the TCR system may provide a high revascularization score. In FIG. 1D, the 3D graphic 130 illustrates the inferior wall and the inferolateral wall. The blockage 135 of the posterior left ventricular (PLV) artery 138 is 100%, and blockages 136 and 137 the distal right coronary artery (RCA) 139 and the distal PDA 140 are 70%. Since the vast majority of the perfusion territory of the PLV artery blockage 135 is not viable, the TCR system may provide a low revascularization score for that blockage. Since the vast majority of perfusion territory of the distal RCA blockage 136 and distal PDA blockage 137 is viable, the TCR system may provide a high revascularization score for each of those blockages.

The TCR system allows a user to rotate the 3D graphic of the heart through any orientation, that is, any spherical angle (e.g., azimuthal angle and polar angle). By rotating the 3D graphic (e.g., using a touchscreen display), the user may better understand relationship between myocardial tissue state, blockage state, and perfusion territories. The 3D graphic may also include a representation of the coronary arteries including those without a blockage. The location of the coronary arteries of a patient may be identified using various techniques such as a coronary angiography, computed tomography (CT) angiography, magnetic resonance angiography (MRA), intravascular ultrasound (IVUS), and optical coherence tomography (OCT). The TCR system may allow the user to select a cardiac chamber to display rather than displaying the entire heart. The TCR system may employ the Blender open-source system to generate, display, and rotate the graphic. (Blender Foundation, Blender, version 2.93, Blender, 2023. [Online]. Available: https://www.blender.org/.) Various techniques for generating a 3D graphic are described in PCT Pub. No. 2023/168017 titled "Overall Ablation Workflow System" and published on Sep. 7, 2023, which is hereby incorporated by reference.

Figure 2:
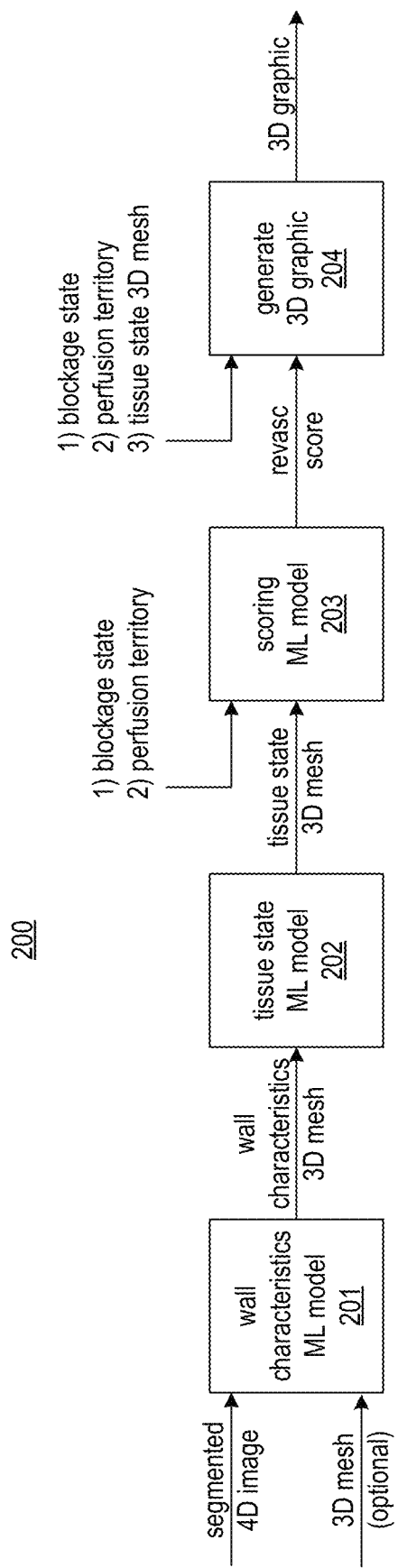
FIG. 2 is a block diagram that illustrates a machine learning implementation of the TCR system in some embodiments.

FIG. 2 is a block diagram that illustrates a machine learning implementation of the TCR system in some embodiments. The ML implementation includes a wall characteristics ML model 201, a tissue state ML model 202, and a scoring ML model 203. The ML implementation generates a tissue state 3D mesh state 3D mesh and the revascularization score (along with the blockage state and the perfusion territory of the blockage) are provided to a generate 3D graphic component to generate a 3D graphic of a heart representing blockage state, revascularization score, perfusion territory, and tissue state. The 3D graphic can then be displayed to help inform treating a patient. The wall characteristics ML model inputs a segmented 4D image and may input a 3D mesh. The wall characteristics ML model may be trained just on segmented 4D images or trained on a combination of 4D images and corresponding 3D meshes. A segmented 4D image and the 3D mesh may be generated as described in Int. Pub. No. WO 2023/168017. The tissue state ML model inputs the wall characteristics 3D mesh and outputs a tissue state 3D mesh. The scoring ML model inputs a tissue state 3D mesh and the blockage state of the blockage and its perfusion territory and generates a revascularization score indicating the benefit of performing a revascularization of the blockage. The generate 3D graphic component inputs a revascularization score and a blockage state, a perfusion territory, and a tissue state 3D mesh. The generate 3D graphics component outputs a 3D graphic of a heart based on the geometry of the tissue state 3D mesh with the blockage and its blockage percentage (or fraction), the perfusion territory, and the revascularization score indicated. The generate graphic 3D component may also input an arterial tree and include an indication of the arterial tree on the 3D graphic. One or more of the ML models may be combined into a single ML model or replaced with a non-ML algorithm. For example, the tissue state ML model may be replaced with an algorithm that calculates a tissue state for each vertex (or each vertex of the epicardium) based on the wall characteristics associated with that vertex.

The ML models may be implemented using various ML architectures. The wall characteristics ML model may be based on a U-net convolutional neural network. The training data for the wall characteristics ML model may be training data sets with segmented 4D images that are each labeled with a wall characteristics 3D mesh. The segmented 4D images may be based on electronic health records (EHRs) that include 4D images (e.g., CT scans). The wall characteristics may be generated using a non-ML algorithm or manually demarcated. The tissue state ML model may be a neural network that inputs a linear representation of the wall characteristics 3D mesh with wall characteristics associated with vertices and outputs a linear representation of the tissue state 3D mesh with tissue state associated with vertices. The scoring ML model may be a neural network that inputs a tissue state 3D mesh that may be annotated with the perfusion territory and the blockage state or as the perfusion territory and blockage state may be separately input. The training data for the scoring ML model may be generated based on EHRs. A training data set includes, for each EHR, a tissue state 3D mesh generated based on a segmented 4D image derived from the EHR and blockage state and perfusion territory derived from the EHR.

Figure 3:
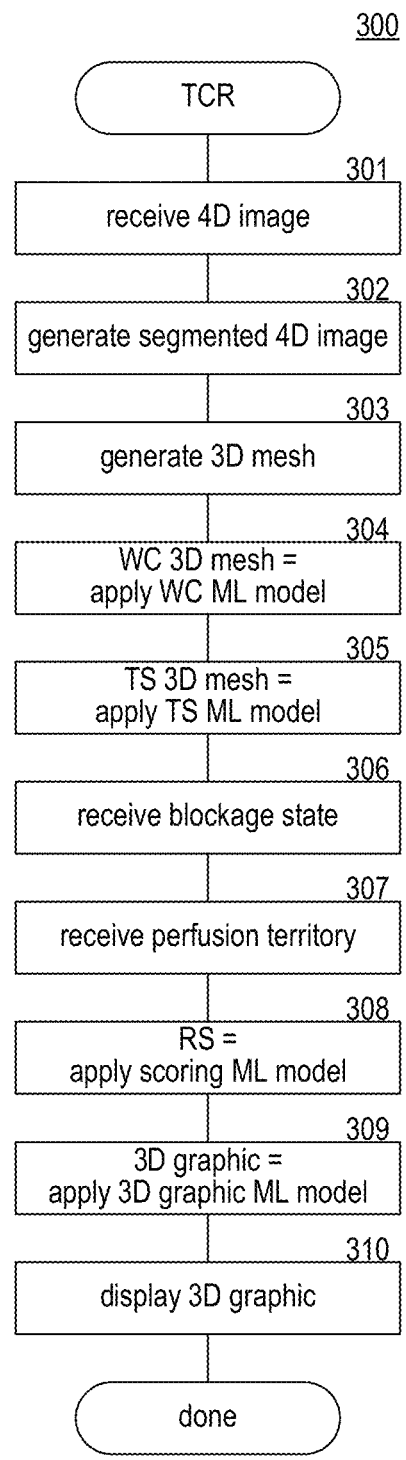
FIG. 3 is a flow diagram that illustrates the processing of a TCR component of the TCR system.

FIG. 3 is a flow diagram that illustrates the processing of a TCR component of the TCR system. In some embodiments, the TCR system 300 generates a 3D graphic of a heart that includes blockage state, revascularization score, tissue state, and perfusion territory of a blockage. In block 301, the component receives a 4D image. In block 302, the component generates a segmented 4D image. In block 303, the component generates a 3D mesh corresponding to the heart or a chamber of the heart based on the segmented 4D image. In block 304, the component applies a wall characteristics ML model to the segmented 4D image and the generated 3D mesh to generate a wall characteristics 3D mesh. In block 305, the component applies a tissue state ML model to the wall characteristics 3D mesh to generate a tissue state 3D mesh. In block 306, the component receives a blockage state of a blockage. In block 307, the component receives a description of the perfusion territory associated with the blockage. In block 308, the component applies a scoring ML model to the blockage state, perfusion territory, and tissue state 3D mesh to generate a revascularization score. In block 309, the component generates the 3D graphic. In block 310, the component displays the 3D graphic. FIGS. 1A-1D are examples of displays of a 3D graphic without the revascularization score indicated. The component then completes.

Figure 4:
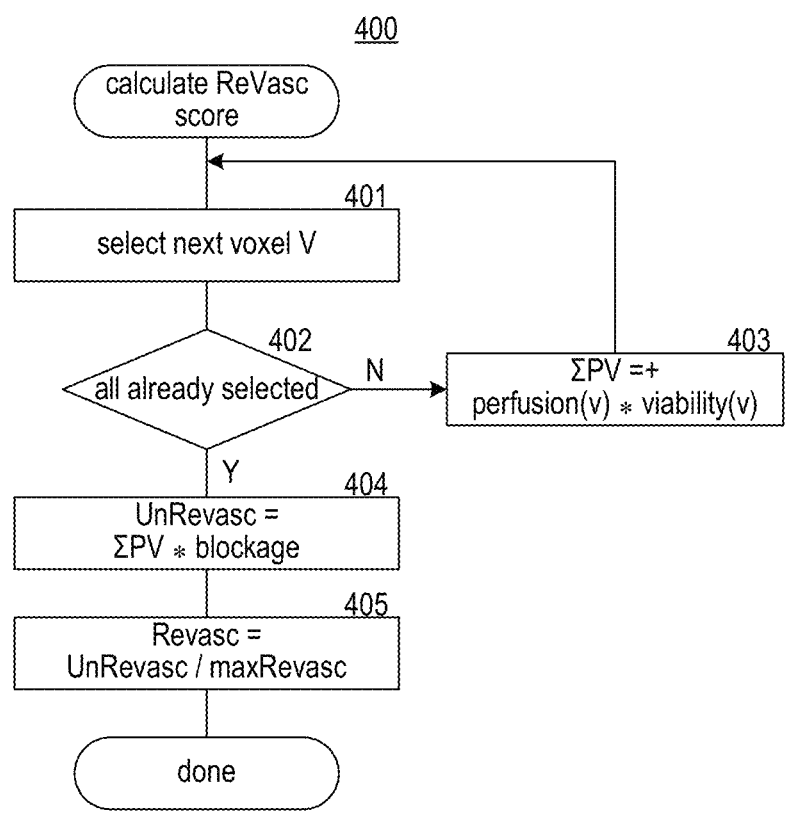
FIG. 4 is a flowchart that illustrates the processing of a calculate revascularization score component of the TCR system.

FIG. 4 is a flowchart that illustrates the processing of a calculate revascularization score component of the TCR system. The calculate revascularization score component 400 implements a non-ML algorithm that generates a revascularization score for a blockage based on its blockage state and its perfusion territory with voxels indicating perfusion fractions and viability scores. In block 401, the component selects the next voxel V. In decision block 402, if all the voxels have already been selected, then the component continues at block 404, else the component continues at block 403. In block 403, the component updates, based on the selected voxel, a sum PV of the products of the perfusion fraction times viability scores and loops to block 401 to select the next voxel. In block 404, the component sets the unnormalized revascularization score to the product of the sum of the products times the blockage fraction. In block 405, the component divides the unnormalized revascularization score by the maximum revascularization score to generate the (normalized) revascularization score and then completes.

Figure 5:
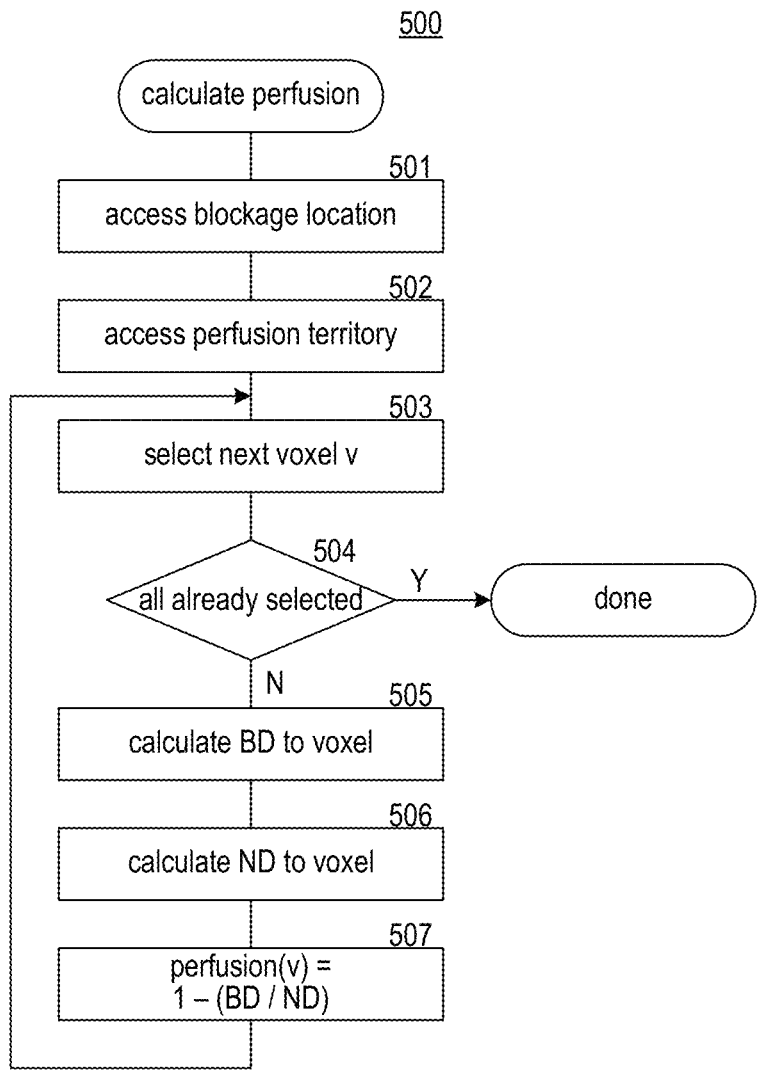
FIG. 5 is a flow diagram that illustrates the processing of a calculate perfusion territory component of the TCR system.

FIG. 5 is a flow diagram that illustrates the processing of a calculate perfusion territory component of the TCR system. The calculate perfusion territory component 500 calculates the perfusion fraction for each voxel in a perfusion territory. In block 501, the component accesses the blockage location of a blockage. In block 502, the component accesses the voxels of the perfusion territory. In block 503, the component selects the next voxel v. In decision block 504, if all the voxels have already been selected, then the component completes, else the component continues at block 505. In block 505, the component calculates the blockage distance BD from the blockage to the voxel. In block 506, the component calculates the neighbor distance ND from the blockage to the closest artery other than the blocked portion of the artery. In block 507, the component sets the perfusion fraction for the selected voxel to one minus the quotient of the blockage distance divided by the sum of the blockage distance plus the neighbor distance. This calculation of perfusion fraction may assume that the perfusion decays linearly based on distance from the blockage, for example, 1−(BD/ND). This example linear decay results in perfusion fractions of 1.0, 0.5, 0.25, and 0.0 the portions of the perfusion territory next to the blockage, halfway between the blockage and the adjacent artery, three quarters the way between the blockage and the adjacent artery, and the next to the nearest artery, respectively. A non-linear decay for the perfusion fraction may employ a square root, for example, 1−sqrt (BD/ND). This non-linear decay results in corresponding perfusion fractions of 1.0, 0.3, 0.13, and 0.0 for the corresponding portions.

The ML models of the TCR system may be any of a variety or combination of supervised, semi-supervised, self-supervised, unsupervised, or reinforcement learning ML models including a neural network such as fully connected, convolutional, recurrent, or autoencoder neural network, or restricted Boltzmann machine, a support vector machine, a Bayesian classifier, k-means clustering, decision tree, generative adversarial networks, transformer, and so on. When the ML model is a deep neural network, the model is trained using training data that includes features derived from data and labels corresponding to the data. For example, the data may be a segmented 4D image with a feature being the segmented 4D image itself, and the labels may be a wall characteristics 3D mesh. The training results in a set of weights for the activation functions of the layers of the deep neural network. The trained deep neural network can then be applied to new data to generate a label for that new data. When the ML model is a support vector machine, a hyper-surface is found to divide the space of possible inputs. For example, the hyper-surface attempts to split the positive examples (e.g., viable tissue in voxels of a segmented 4D image) from the negative examples (e.g., diseased viable in voxels of the segmented 4D image) by maximizing the distance between the nearest of the positive and negative examples to the hyper-surface. The trained support vector machine can then be applied to a segmented 4D image of a patient to generate the tissue state for voxels. The tissue state 3D mesh may be derived from those tissue states. An ML model may generate values of discrete domain (e.g., classification), probabilities, and/or values of a continuous domain (e.g., regression value, classification probability).

The TCR system may employ various techniques that can be used to train a support vector machine such as adaptive boosting, which is an iterative process that runs multiple tests on a collection of training data. Adaptive boosting transforms a weak learning algorithm (an algorithm that performs at a level only slightly better than chance) into a strong learning algorithm (an algorithm that displays a low error rate). The weak learning algorithm is run on different subsets of the training data. The algorithm concentrates increasingly on those examples in which its predecessors tended to show mistakes. The algorithm corrects the errors made by earlier weak learners. The algorithm is adaptive because it adjusts to the error rates of its predecessors. Adaptive boosting combines rough and moderately inaccurate rules of thumb to create a high-performance algorithm. Adaptive boosting combines the results of each separately run test into a single, very accurate classifier. Adaptive boosting may use weak classifiers that are single-split trees with only two leaf nodes.

The TCR system may employ a neural network model has three major components: architecture, loss function, and search algorithm. The architecture defines the functional form relating the inputs to the outputs (in terms of network topology, unit connectivity, and activation functions). The search for a set of weights that minimizes the loss function is the training process. A neural network model may use a radial basis function (RBF) network and a standard or stochastic gradient descent as the search technique with backpropagation.

The wall characteristics ML model may be a convolutional neural network (CNN) that inputs a 4D image and outputs a wall characteristics 3D mesh. A CNN has multiple layers such as a convolutional layer, a rectified linear unit (ReLU) layer, a pooling layer, a fully connected (FC) layer, and so on. Some more complex CNNs may have multiple convolutional layers, pooling layers, and FC layers. Each layer includes a collection of neurons. A neuron inputs output of prior layers (or original input) and applies an activation function to the inputs to generate an output.

A convolutional layer may include multiple filters (also referred to as kernels or activation functions). A filter inputs a convolutional window, for example, of an image that is a 2D slice of a 3D image of a 4D image, applies weights to each pixel of the convolutional window, and outputs a value for that convolutional window. For example, if the 1024×1024 pixels, the convolutional window may be 8 by 8 pixels. The filter may apply a different weight to each of the 64 pixels in a convolutional window to generate the value.

An activation function has a weight for each input and generates an output by combining the inputs based on the weights. The activation function may be a rectified ReLU that sums the values of each input times its weight to generate a weighted value and outputs max (0,weighted value) to ensure that the output is not negative. The weights of the activation functions are learned when training a ML model. The ReLU function of max (0,weighted value) may be represented as a separate ReLU layer with a neuron for each output of the prior layer that inputs that output and applies the ReLU function to generate a corresponding "rectified output."

A pooling layer may be used to reduce the size of the outputs of the prior layer by downsampling the outputs. For example, each neuron of a pooling layer may input 16 outputs of the prior layer and generate one output resulting in a 16-to-1 reduction in outputs.

An FC layer includes neurons that each input all the outputs of the prior layer and generates a weighted combination of those inputs. For example, if the penultimate layer generates 256 outputs and the FC layer inputs a neuron for each of three classifications (e.g., viable tissue, diseased tissue, non-viable tissue), each neuron inputs the 256 outputs and applies weights to generate value for its classification.

The TCR system may employ a variational autoencoder (VAE) to generate, for each 3D cardiac image of 4D cardiac image, a latent vector representing that 3D cardiac images. The latent vectors can be then input to, for example, a neural network which outputs a 3D mesh indicating the wall characteristics.

In some embodiments, the TCR system may employ a diffusion ML model to generate additional training data using a generative process. (See, Rombach, R., Blattmann, A., Lorenz, D., Esser, P. and Ommer, B., 2022. High-resolution image synthesis with latent diffusion models. In Proceedings of the IEEE/CVF conference on computer vision and pattern recognition (pp. 10684-10695), which is hereby incorporated by reference.) A diffusion ML model is a generative ML model that inputs noisy data and progressively denoises the data until the denoised data appears to be indistinguishable from real data such as a CT scan. A diffusion ML model is trained using a forward diffusion process that successively adds noise to input training data such as a 4D image to generate noisy data and a reverse diffusion process that successively denoises the noisy data to generate denoised data that approximates the input training data. The training learns weights for the reverse diffusion process that tend to minimize the difference between the input training data and the denoised data.

The TCR system may train the diffusion model to generate additional training data for the wall characteristics ML model that are 4D images and 3D meshes with wall characteristics 3D meshes as "conditioning" (described below). The training data for the diffusion model may be generated using an initial wall characteristics ML model trained using training data derived from EHRs or a non-ML algorithm. To train the diffusion model, the 4D images and 3D meshes are input to the forward diffusion process and the associated wall characteristics 3D meshes input as "conditioning" (which is described below) to the reverse diffusion process.

The tissue state ML model and the scoring ML model may be trained using a similar approach. For example, to generate additional training data for the tissue state ML model, wall characteristics 3D meshes (generated by the trained wall characteristics 3D model) are input to the initially trained tissue state ML model to generate tissue state 3D meshes. To train the diffusion model, the wall characteristics 3D meshes are input to the forward diffusion process and the tissue state 3D meshes are input as conditioning. The tissue state 3D meshes may be generated using an initially trained tissue state ML model or a non-ML algorithm.

After a diffusion model is trained, the reverse diffusion process is employed to generate training data that can be used to train the wall characteristics ML model or the other ML models. To do so, randomly generated noisy data and conditioning data is input to the reverse diffusion process. For example, the conditioning data for the wall characteristics ML model may be wall characteristics 3D meshes that may be variations of wall characteristics 3D meshes used as training data for the initial wall characteristics ML model.

The forward diffusion process employs a Markov chain that incrementally adds Gaussian noise to the training data over a series of steps. This process transforms the training data from its initial distribution to a Gaussian distribution. The reverse diffusion process employs a neural network to incrementally approximate and remove the noise that was added at each step of the forward diffusion process. When generating data, randomly generated noisy data is input to the reverse diffusion process which incrementally removes the noise that was learned during training.

The forward diffusion process systematically adds Gaussian noise to the original data $x_0$ Gaussian noise over T timesteps, resulting in a sequence of increasingly noisy data $x_1, x_2, \ldots, x_T$. The process at each time step t may be represented by the equation:

$$x_t = \sqrt{\alpha_t} x_{t-1} + \sqrt{1-\alpha_t} \varepsilon_t \in N(0, I)$$

where $x_t$ is data at timestep t, $\varepsilon_t$ is Gaussian noise, $\alpha_t$ is the amount of noise added, and I is the identity matrix.

The reverse diffusion process learns the distribution of the training data by starting from noise and progressively denoising it over the timesteps. The training estimates the reverse of the forward diffusion process using a neural network that may be represented by the equation:

$$x_{t-1} = \frac{1}{\sqrt{\alpha_t}} \left( x_t - \frac{1-\alpha_t}{\sqrt{1-\bar{\alpha}_t}} f_\theta(x_t, t) \right)$$

where $$\bar{\alpha}_t = \prod_{i=1}^{t} \alpha_i$$

represent the cumulative noise and $f_\theta(x_t, t)$ represents the neural network.

The goal of training a diffusion model is to minimize the difference between the original data and the data reconstructed by the reverse diffusion process using a loss function that may be represented by the equation.

$$L(\theta) = E_{x_0, \varepsilon_t, t}[\|Et - f_\theta(x_t, t)\|^2].$$

The computing systems (e.g., network nodes or collections of network nodes) on which the TCR system and the other described systems may be implemented may include a central processing unit, input devices, output devices (e.g., display devices and speakers), storage devices (e.g., memory and disk drives), network interfaces, graphics processing units, communications links (e.g., Ethernet, Wi-Fi, cellular, and Bluetooth), global positioning system devices, and so on. The input devices may include keyboards, pointing devices, touch screens, gesture recognition devices (e.g., for air gestures), head and eye tracking devices, microphones for voice recognition, and so on. The computing systems may include high-performance computing systems, distributed systems, cloud-based computing systems, client computing systems that interact with cloud-based computing system, desktop computers, laptops, tablets, e-readers, personal digital assistants, smartphones, gaming devices, servers, and so on. The computing systems may access computer-readable media that include computer-readable storage mediums and data transmission mediums. The computer-readable storage mediums are tangible storage means that do not include a transitory, propagating signal. Examples of computer-readable storage mediums include memory such as primary memory, cache memory, and secondary memory (e.g., DVD), and other storage. The computer-readable storage media may have recorded on them or may be encoded with computer-executable instructions or logic that implements the TCR system and the other systems described. The data transmission media are used for transmitting data via transitory, propagating signals or carrier waves (e.g., electromagnetism) via a wired or wireless connection. The computing systems may include a secure crypto processor as part of a central processing unit (e.g., Intel Secure Guard Extension (SGX)) for generating and securely storing keys and for encrypting and decrypting data using the keys and for securely executing all or some of the computer-executable instructions of the TCR system. Some of the data sent by and received by the TCR system may be encrypted, for example, to preserve patient privacy (e.g., to comply with government regulations such the European General Data Protection Regulation (GDPR) or the Health Insurance Portability and Accountability Act (HIPAA) of the United States). The TCR system may employ asymmetric encryption (e.g., using private and public keys of the Rivest-Shamir-Adleman (RSA) standard) or symmetric encryption (e.g., using a symmetric key of the Advanced Encryption Standard (AES)).

The one or more computing systems may include client-side computing systems and cloud-based computing systems (e.g., public or private) that each executes computer-executable instructions of the TCR system. A client-side computing system may send data to and receive data from one or more servers of the cloud-based computing systems of one or more cloud data centers. For example, a client-side computing system may send a request to a cloud-based computing system to perform tasks such as run generate a 3D graphic or train an ML model. A cloud-based computing system may respond to the request by sending to the client-side computing system data derived from performing the task. The servers may perform computationally expensive tasks in advance of processing by a client-side computing system such as training a ML model or in response to data received from a client-side computing system. A client-side computing system may provide a user experience (e.g., user interface) to a user of the TCR system. The user experience may originate from a client computing device or a server computing device. Alternatively, a cloud-based computing system may generate the graphic (e.g., in a Hyper-Text Markup Language (HTML) format or an extensible Markup Language (XML) format) and provide it to the client-side computing system for display. A client-side computing system (e.g., in a hospital) may also send data to and receive data from various medical devices such as a CT scanner. The data received from the medical devices may include a 4D image. The data may be in a Digital Imaging and Communications in Medicine (DICOM) format. A client-side computing device may also send data to and receive data from medical computing systems that store patient medical history data, descriptions of medical devices (e.g., type, manufacturer, and model number) of a medical facility, that store, medical facility device descriptions, that store results of procedures, and so on. The term cloud-based computing system may encompass computing systems of a public cloud data center provided by a cloud provider (e.g., Azure provided by Microsoft Corporation) or computing systems of a private server farm (e.g., operated by the provider of the TCR system).

The TCR system and the other described systems may be described in the general context of computer-executable instructions, such as program modules and components, executed by one or more computers, processors, or other devices. Generally, program modules or components include routines, programs, objects, data structures, and so on that perform tasks or implement data types of the TCR system and the other described systems. Typically, the functionality of the program modules may be combined or distributed as desired in various examples. Aspects of the TCR system and the other described systems may be implemented in hardware using, for example, an application-specific integrated circuit (ASIC) or a field programmable gate array (FPGA).

The following paragraphs describe various aspects of the TCR system. An implementation of the TCR system may employ any combination or sub-combination of the aspects and may employ additional aspects. The processing of the aspects may be performed by one or more computing systems with one or more processors that execute computer-executable instructions that implement the aspects and that are stored on one or more computer-readable storage mediums.

In some aspects, the techniques described herein relate to a method performed by one or more computing systems for generating a revascularization score for a blockage of a coronary artery of the heart a patient, the method including: determining myocardial tissue state of the myocardium of the heart, the myocardial tissue state indicating viability of the myocardial tissue; accessing an indication of a blockage state of a blockage of a coronary artery of the patient, the blockage state indicating a blockage location and a blockage amount of the blockage; accessing an indication of a perfusion territory of myocardial tissue; generating a revascularization score for the blockage based on myocardial tissue state, the blockage state, and the perfusion territory; generating a graphic of the heart that indicates one or more of the coronary arteries, the myocardial tissue state, the blockage state, and the revascularization score; and displaying the graphic. In some aspects, the techniques described herein relate to a method further applying machine learning (ML) to a 4D image of the heart to determine the myocardial tissue state. In some aspects, the techniques described herein relate to a method wherein the application of the ML includes applying a wall characteristics ML model to the 4D image to generate a wall characteristics 3D mesh and applying a tissue state ML model to the wall characteristics 3D mesh to generate a tissue state 3D mesh. In some aspects, the techniques described herein relate to a method wherein the wall characteristics ML model and/or the tissue state ML model are based on a graph neural network. In some aspects, the techniques described herein relate to a method wherein the perfusion territory specifies perfusion factors for locations within the perfusion territory. In some aspects, the techniques described herein relate to a method further including accessing a 3D image of the heart; generating a segmentation of the heart based on the 3D image; and generating a 3D mesh representing the heart. In some aspects, the techniques described herein relate to a method wherein vertices of the 3D mesh are associated with features of the myocardial tissue state, the blockage state, and perfusion territory. In some aspects, the techniques described herein relate to a method wherein the perfusion territory is patient-specific. In some aspects, the techniques described herein relate to a method wherein the patient-specific perfusion territory for a blockage is derived from a coronary arterial tree is identified from an angiogram, the coronary arterial tree identifies paths of coronary arteries and their diameters. In some aspects, the techniques described herein relate to a method wherein the coronary arterial tree is identified using a machine learning (ML) model that is a convolutional neural network that inputs an angiogram and outputs a coronary arterial tree. In some aspects, the techniques described herein relate to a method further including determining the perfusion territory for the blockage based on the diameter of the coronary artery at the blockage location, the diameter of an adjacent coronary artery, and distance between the blockage location and the adjacent coronary artery. In some aspects, the techniques described herein relate to a method further including calculating perfusion factors for myocardial tissue within the perfusion territory that indicates the amount of perfusion of the myocardial tissue that would be provided from the blockage location assuming there was no blockage. In some aspects, the techniques described herein relate to a method wherein the revascularization score is based on improvement of perfusion to the perfusion territory after revascularization factoring the amount of viable, diseased viable, and non-viable myocardial tissue in the perfusion territory and a perfusion factor for the myocardial tissue that indicates the amount of perfusion of the myocardial tissue that would be provided from the blockage location assuming there was no blockage. In some aspects, the techniques described herein relate to a method wherein the graphic further indicates the perfusion territory. In some aspects, the techniques described herein relate to a method wherein the myocardial tissue state is based on wall thickness of the heart wall of the patient.

In some aspects, the techniques described herein relate to one or more computing systems for generating a revascularization score for a blockage of a coronary artery of the heart a patient, the one or more computing systems including: one or more computer-readable storage mediums that store: myocardial tissue state of the myocardium of the heart, the myocardial tissue state indicating viability of the myocardial tissue; blockage state of a blockage of a coronary artery of the patient, the blockage state indicating a blockage location and a blockage amount of the blockage; perfusion territory of myocardial tissue indicating perfusion provided to the myocardial tissue by blood flowing through the blockage location assuming no blockage; and computer-executable instructions for controlling the one or more computing systems to generate a revascularization score for the blockage based on myocardial tissue state, the blockage state, and the perfusion territory, the revascularization score providing an assessment of benefit resulting from the revascularization of the blockage; and one or more processors for controlling the one or more computing systems to execute one or more of the computer-executable instructions. In some aspects, the techniques described herein relate to one or more computing systems wherein the instructions further include instructions to: generating a 3D graphic of the heart with indications one or more of the coronary arteries, the myocardial tissue state, the blockage state, the revascularization score, and the perfusion territory; and displaying the 3D graphic. In some aspects, the techniques described herein relate to one or more computing systems wherein a user can indicate to rotate in 3D graphic to change the view of heart that the 3D graphic represents. In some aspects, the techniques described herein relate to one or more computing systems wherein the instructions further include instructions to apply machine learning (ML) to a 4D image of the heart to determine the myocardial tissue state. In some aspects, the techniques described herein relate to one or more computing systems wherein the application of the ML includes applying a wall characteristics ML model to the 4D image to generate a wall characteristics 3D mesh and applying a tissue state ML model to the wall characteristics 3D mesh to generate a tissue state 3D mesh. In some aspects, the techniques described herein relate to one or more computing systems wherein the wall characteristics ML model and/or the tissue state ML model are based on a graph neural network. In some aspects, the techniques described herein relate to one or more computing systems wherein the perfusion territory specifies perfusion factors for locations within the perfusion territory. In some aspects, the techniques described herein relate to one or more computing systems wherein the perfusion territory is patient-specific. In some aspects, the techniques described herein relate to one or more computing systems wherein the patient-specific perfusion territory for a blockage is derived from a coronary arterial tree is identified from an angiogram, the coronary arterial tree identifies paths of coronary arteries and their diameters. In some aspects, the techniques described herein relate to one or more computing systems wherein the instructions further include instructions to determine the perfusion territory for the blockage based on the diameter of the coronary artery at the blockage location, the diameter of an adjacent coronary artery, and distance between the blockage location and the adjacent coronary artery. In some aspects, the techniques described herein relate to one or more computing systems wherein the instructions include further instructions to calculate perfusion factors for myocardial tissue within the perfusion territory that indicates the amount of perfusion of the myocardial tissue that would be provided from the blockage location assuming there was no blockage. In some aspects, the techniques described herein relate to one or more computing systems wherein the myocardial tissue state is based on wall thickness of the heart wall of the heart.

In some aspects, the techniques described herein relate to one or more computer-readable storage mediums storing computer-executable instructions for controlling one or more computing systems to perform a method including: determining myocardial tissue state of the myocardium of the heart of a patient, the myocardial tissue state indicating viability of the myocardial tissue; determining a blockage state of a blockage of a coronary artery of the patient, the blockage state indicating a blockage location and a blockage amount of the blockage; determining an indication of a perfusion territory of myocardial tissue; generating a revascularization score for the blockage based on myocardial tissue state, the blockage state, and the perfusion territory, the revascularization score providing an assessment of benefit of revascularization based on the blockage; and outputting an indicating of the revascularization score.

In some aspects, the techniques described herein relate to one or more computing systems for generating a revascularization score for a blockage of a coronary artery of the heart a patient, the one or more computing systems including: one or more computer-readable storage mediums that store: wall thickness of the heart wall of the heart of the patient; and blockage state of a blockage of a coronary artery of the patient, the blockage state indicating a blockage location and a blockage amount of the blockage; and computer-executable instructions for controlling the one or more computing systems to generate a revascularization score for the blockage based on wall thickness of the wall thickness and the blockage state, the revascularization score providing an assessment of benefit resulting from the revascularization of the blockage; and one or more processors for controlling the one or more computing systems to execute one or more of the computer-executable instructions. In some aspects, the techniques described herein relate to one or more computing systems wherein one or more computer-readable storage mediums further store perfusion territory of myocardial tissue indicating perfusion provided to the myocardial tissue by blood flowing through the blockage location assuming no blockage wherein the generating of the revascularization score is further based on the perfusion territory.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims.

We claim:

1. A method performed by one or more computing systems for generating a revascularization score for a blockage of a coronary artery of the heart of a patient, the method comprising:
   accessing myocardial tissue state of the myocardium of the heart, the myocardial tissue state indicating viability of the myocardial tissue;
   accessing an indication of a blockage state of a blockage of a coronary artery of the patient, the blockage state indicating a blockage location and a blockage amount of the blockage;
   accessing an indication of a perfusion territory of the blockage, the perfusion territory being the myocardial tissue that is perfused by normal blood flow with no blockage through the blockage location;
   generating a three-dimensional (3D) mesh based on imaging of the heart, the 3D mesh representing voxels within the myocardium of the heart;
   for each of a plurality of voxels within the perfusion territory, associating that voxel with a myocardial tissue state;
   generating a revascularization score for the blockage based on myocardial tissue state associated with the voxels within the perfusion territory and-the blockage state, the revascularization score providing an assessment of benefit to myocardial tissue resulting from the revascularization of the blockage;

generating a graphic of the heart based on the 3D mesh that indicates one or more of the coronary arteries, the myocardial tissue state within the perfusion territory, the blockage state, and the revascularization score; and displaying the graphic.

2. The method of claim 1 further applying machine learning (ML) to a four-dimensional (4D) image of the heart to determine the myocardial tissue state.

3. The method of claim 2 wherein the application of the ML includes applying a wall characteristics ML model to the 4D image to generate a wall characteristics 3D mesh and applying a tissue state ML model to the wall characteristics 3D mesh to generate a tissue state 3D mesh.

4. The method of claim 3 wherein the wall characteristics ML model and/or the tissue state ML model are based on a graph neural network.

5. The method of claim 1 wherein the perfusion territory specifies perfusion factors for locations within the perfusion territory.

6. The method of claim 1 further comprising:
accessing a 3D image of the heart;
generating a segmentation of the heart based on the 3D image; and
generating a 3D mesh representing the heart.

7. The method of claim 6 wherein vertices of the 3D mesh are associated with features of the myocardial tissue state, the blockage state, and perfusion territory.

8. The method of claim 1 wherein the perfusion territory is patient-specific and the patient-specific perfusion territory for a blockage is derived from a coronary arterial tree as identified from an angiogram, the coronary arterial tree identifies paths of coronary arteries and their diameters.

9. The method of claim 8 wherein the coronary arterial tree is identified using a machine learning (ML) model that is a convolutional neural network that inputs an angiogram and outputs a coronary arterial tree.

10. The method of claim 1 further comprising determining the perfusion territory for the blockage based on the diameter of the coronary artery at the blockage location, the diameter of an adjacent coronary artery, and distance between the blockage location and the adjacent coronary artery.

11. The method of claim 10 further comprising calculating perfusion factors for myocardial tissue within the perfusion territory that indicate the amount of perfusion of the myocardial tissue that would be provided from the blockage location assuming there was no blockage.

12. The method of claim 1 wherein the revascularization score is based on improvement of perfusion to the perfusion territory after revascularization factoring the amount of viable, diseased viable, and non-viable myocardial tissue in the perfusion territory and a perfusion factor for the myocardial tissue that indicates the amount of perfusion of the myocardial tissue that would be provided from the blockage location assuming there was no blockage.

13. The method of claim 1 wherein the graphic further indicates the perfusion territory.

14. The method of claim 1 further comprising training a scoring machine learning (ML) model using training data that includes training data sets that each has a feature vector and a label, the feature vector having features of a blockage that include blockage state and, for voxels within the perfusion territory, a viability score and a perfusion factor, the label indicating a revascularization score.

15. The method of claim 14 wherein the revascularization score for a training data set is calculated using a non-ML algorithm.

16. The method of claim 14 wherein the generating of the revascularization score includes applying the scoring ML model to a feature vector with features of the blockage of the patient that include blockage state and for voxels within the perfusion territory of the patient, a viability score and a perfusion factor.

17. The method of claim 1 wherein the generating of the revascularization score includes applying a scoring machine learning (ML) model that outputs a revascularization score based on a feature vector with features of the blockage that include blockage state and for voxels within the perfusion territory, a viability score and a perfusion factor.

18. One or more computing systems for generating a revascularization score for a blockage of a coronary artery of the heart a patient, the one or more computing systems comprising:
one or more computer-readable storage mediums that store:
myocardial tissue state of the myocardium of the heart, the myocardial tissue state indicating viability of the myocardial tissue;
blockage state of a blockage of a coronary artery of the patient, the blockage state indicating a blockage location and a blockage amount of the blockage;
perfusion territory of myocardial tissue indicating perfusion provided to the myocardial tissue by blood flowing through the blockage location assuming no blockage; and
computer-executable instructions for controlling the one or more computing systems to:
generate a three-dimensional (3D) mesh based on imaging of the heart, the 3D mesh representing voxels within the myocardium of the heart;
for each of a plurality of voxels within the perfusion territory associate that voxel with a myocardial tissue state; and
generate a revascularization score for the blockage based on myocardial tissue state associated with the voxels within the perfusion territory and, the blockage state, the revascularization score providing an assessment of benefit to myocardial tissue resulting from the revascularization of the blockage; and
one or more processors for controlling the one or more computing systems to execute one or more of the computer-executable instructions.

19. The one or more computing systems of claim 18 wherein the instructions further include instructions to:
generating a 3D graphic of the heart based on the 3D mesh with indications of one or more of the coronary arteries, the myocardial tissue state, the blockage state, the revascularization score, and the perfusion territory; and
displaying the 3D graphic.

20. The one or more computing systems of claim 19 wherein a user can indicate to rotate the 3D graphic to change the view of the heart that the 3D graphic represents.

21. The one or more computing systems of claim 18 wherein the instructions further include instructions to apply machine learning (ML) to a 4D image of the heart to determine the myocardial tissue state.

22. The one or more computing systems of claim 21 wherein the application of the ML includes applying a wall characteristics ML model to the 4D image to generate a wall characteristics 3D mesh and applying a tissue state ML model to the wall characteristics 3D mesh to generate a tissue state 3D mesh.

23. The one or more computing systems of claim 22 wherein the wall characteristics ML model and/or the tissue state ML model are based on a graph neural network.

24. The one or more computing systems of claim 18 wherein the perfusion territory specifies perfusion factors for locations within the perfusion territory.

25. The one or more computing systems of claim 18 wherein the perfusion territory is patient-specific.

26. The one or more computing systems of claim 25 wherein the patient-specific perfusion territory for a blockage is derived from a coronary arterial tree is identified from an angiogram, the coronary arterial tree identifies paths of coronary arteries and their diameters.

27. The one or more computing systems of claim 18 wherein the instructions further include instructions to determine the perfusion territory for the blockage based on the diameter of the coronary artery at the blockage location, the diameter of an adjacent coronary artery, and distance between the blockage location and the adjacent coronary artery.

28. The one or more computing systems of claim 27 wherein the instructions include further instructions to calculate perfusion factors for myocardial tissue within the perfusion territory that indicate the amount of perfusion of the myocardial tissue that would be provided from the blockage location assuming there was no blockage.

29. The one or more computing systems of claim 18 wherein the myocardial tissue state is based on wall thickness of the heart wall of the heart.

30. One or more computer-readable storage mediums storing computer-executable instructions for controlling one or more computing systems to perform a method comprising:

accessing myocardial tissue state of the myocardium of the heart of a patient, the myocardial tissue state indicating viability of the myocardial tissue;

determining a blockage state of a blockage of a coronary artery of the patient, the blockage state indicating a blockage location and a blockage amount of the blockage;

accessing an indication of a perfusion territory of the blockage, the perfusion territory being the myocardial tissue that is perfused by normal blood flow with no blockage through the blockage location;

generating a three-dimensional (3D) mesh based on imaging of the heart, the 3D mesh representing voxels within the myocardium of the heart;

for each of a plurality of voxels within the perfusion territory, associating that voxel with a myocardial tissue state;

generating a revascularization score for the blockage based on myocardial tissue state associated with the voxels within the perfusion territory and the blockage state, the revascularization score providing an assessment of benefit to myocardial tissue resulting from the revascularization of the blockage; and outputting an indicating of the revascularization score.

* * * * *